United States Patent [19]
Herron et al.

[11] Patent Number: 5,512,492
[45] Date of Patent: Apr. 30, 1996

[54] WAVEGUIDE IMMUNOSENSOR WITH COATING CHEMISTRY PROVIDING ENHANCED SENSITIVITY

[75] Inventors: James N. Herron; Douglas A. Christensen; Karin D. Caldwell, all of Salt Lake City, Utah; Vera Janatová, Prague, Czechoslovakia; Shao-Chie Huang; Hsu-Kun Wang, both of Salt Lake City, Utah

[73] Assignee: University of Utah Research Foundation, Salt Lake City, Utah

[21] Appl. No.: 64,608

[22] Filed: May 18, 1993

[51] Int. Cl.$^6$ .................... G01N 33/543; G01N 33/544; G01N 33/552
[52] U.S. Cl. .............. 436/518; 356/317; 356/318; 356/244; 356/246; 385/12; 385/129; 385/130; 422/57; 422/58; 422/82.05; 422/82.08; 422/82.11; 427/162; 435/7.5; 435/287.2; 435/287.9; 435/808; 436/164; 436/527; 436/531; 436/805
[58] Field of Search ................ 356/317, 318, 356/244, 246; 385/12, 129, 130; 422/57, 58, 82.05, 82.08, 82.11; 435/7.5, 287, 291, 808; 436/512, 518, 524, 527, 528, 531, 532, 547, 548, 164, 165, 172, 805, 807, 809; 427/162

[56] References Cited

U.S. PATENT DOCUMENTS

| | | | |
|---|---|---|---|
| Re. 33,064 | 9/1989 | Carter | 436/34 |
| Re. 34,394 | 9/1993 | Bunting | 436/500 |
| 3,939,350 | 2/1976 | Kronick et al. | 356/36 |
| 4,166,105 | 8/1979 | Hirschfeld | 424/12 |
| 4,235,869 | 11/1980 | Schwarzberg | 424/12 |
| 4,264,766 | 4/1981 | Fischer | 424/12 |
| 4,298,685 | 11/1981 | Parikh et al. | 435/810 |
| 4,429,008 | 1/1984 | Martin et al. | 436/532 |
| 4,447,546 | 5/1984 | Hirschfeld | 436/527 |
| 4,450,231 | 5/1984 | Ozkan | 436/506 |
| 4,558,014 | 12/1985 | Hirschfeld et al. | 436/527 |
| 4,596,723 | 6/1986 | Kaufman et al. | 427/336 |
| 4,708,871 | 11/1987 | Geysen | 424/88 |
| 4,775,637 | 10/1988 | Sutherland et al. | 436/527 |
| 4,810,658 | 3/1989 | Shanks et al. | 436/172 |

(List continued on next page.)

FOREIGN PATENT DOCUMENTS

| | | |
|---|---|---|
| 0478137 | 1/1992 | European Pat. Off. . |
| 8909408 | 10/1989 | WIPO . |
| 9113339 | 9/1991 | WIPO . |
| 9216838 | 10/1992 | WIPO . |

OTHER PUBLICATIONS

Lee, Jin Ho; Kopecek, J. and Andrade, J. D., "Protein-resistant surfaces prepared by PEO-containing block copolymer surfactants", Journal of Biomedical Materials Research, Published by John Wiley & Sons, pp. 351–368 (1989).

Carlsson, J.; Drevin, K. and Axen, R., "Protein Thiolation and Reversible Protein-Protein Conjugation", Biochem. J. (1978) 173, 723–737, Printed in Great Britain.

Ives, Jeffrey T., "Optical waveguide sensors: characterization of evanescent and scatter excitation," Ph.D. dissertation submitted to Department of Bioengineering, University of Utah, Jun. 1990.

Master's Thesis, Shao-Chie Huang, Nov. 1991.

Huang, Shao-Chie, "PEG derivatives as tethers for site-directed immobilization of oxidized antibody," title page, abstract (pp. iv–v), and pp. 35–39.

*Primary Examiner*—David Saunders
*Assistant Examiner*—Christopher L. Chin
*Attorney, Agent, or Firm*—Trask, Britt & Rossa

[57] ABSTRACT

Methods and apparatus for evanescent light fluoroimmunoassays are disclosed. The apparatus employs a planar waveguide and optionally has multi-well features and improved evanescent field intensity. The preferred biosensor and assay method have the capture molecules immobilized to the waveguide surface by site-specific coupling chemistry. Additionally, the coatings used to immobilize the capture molecules provide reduced non-specific protein adsorption.

31 Claims, 9 Drawing Sheets

U.S. PATENT DOCUMENTS

| | | | |
|---|---|---|---|
| 4,820,649 | 4/1989 | Kawaguchi et al. | 422/57 |
| 4,852,967 | 8/1989 | Cook et al. | 350/96.15 |
| 4,880,752 | 11/1989 | Keck | 422/59 |
| 4,909,990 | 3/1990 | Block et al. | 422/82.11 |
| 4,978,503 | 12/1990 | Shanks et al. | 422/82.11 |
| 5,006,333 | 4/1991 | Seifer et al. | 435/180 |
| 5,043,278 | 8/1991 | Nagaoka et al. | 435/181 |
| 5,061,857 | 10/1991 | Thompson et al. | 250/458.1 |
| 5,071,217 | 12/1991 | Birch | 385/33 |
| 5,081,012 | 1/1992 | Flanagan et al. | 422/82.11 |
| 5,156,976 | 10/1992 | Slovacek et al. | 436/172 |
| 5,166,515 | 11/1992 | Attridge | 356/246 |
| 5,168,537 | 12/1992 | Rajasekharan et al. | 385/88 |
| 5,182,216 | 1/1993 | Clayton et al. | 436/518 |
| 5,192,502 | 3/1993 | Attridge | 422/57 |
| 5,248,620 | 9/1993 | Sluka et al. | 436/817 |
| 5,344,784 | 9/1994 | Attridge | 422/58 |

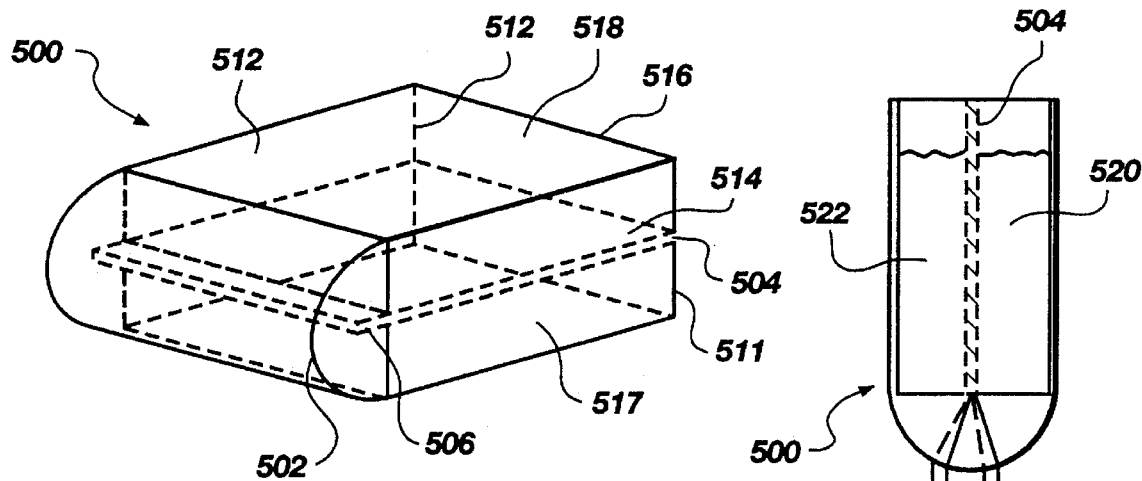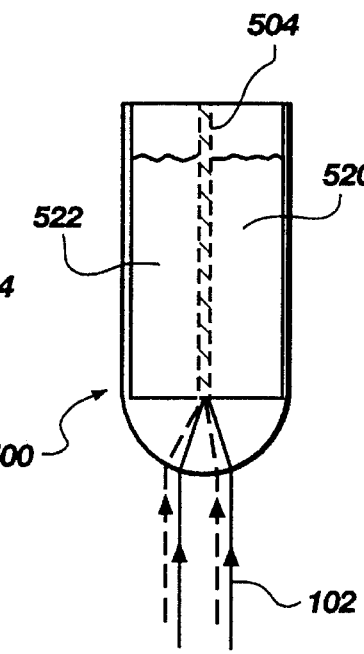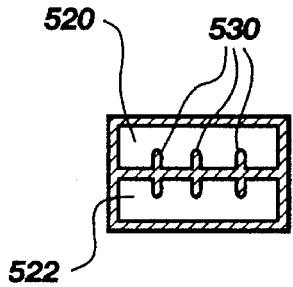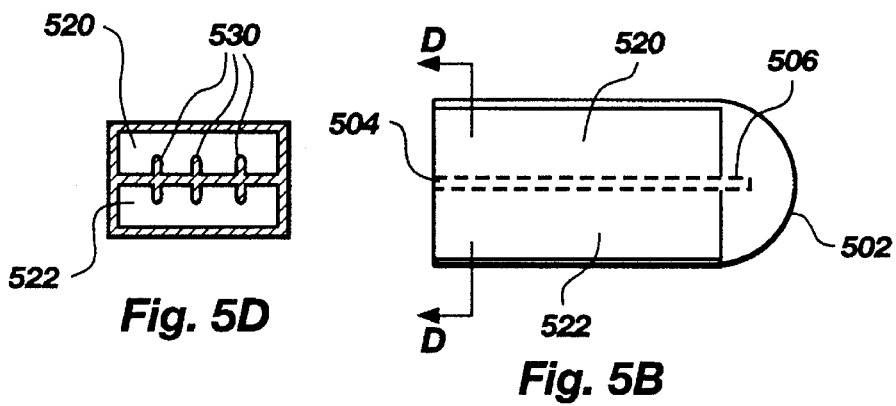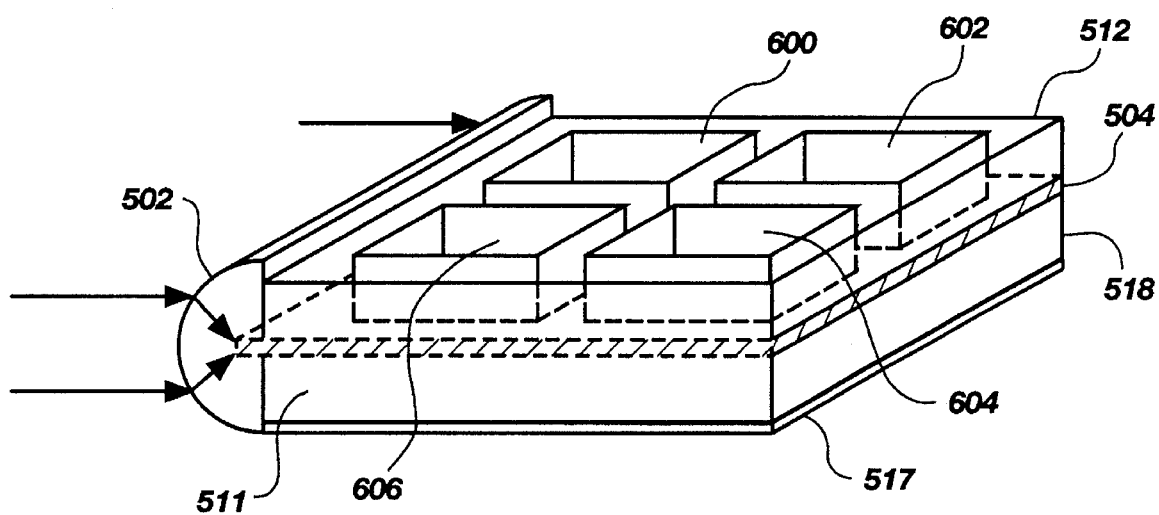

WAVEGUIDE IMMUNOSENSOR WITH COATING CHEMISTRY PROVIDING ENHANCED SENSITIVITY

BACKGROUND OF THE INVENTION

1. Field

This application relates to the art of analyzing samples for particular substances by means of fluorescent binding assays, and more particularly to apparatus, compositions and methods for such assays employing evanescent light.

2. State of the Art

Biosensor apparatus based on optical detection of analytes by fluorescence of tracer molecules, have attracted increasing attention in recent years. Such apparatus are useful for both diagnostic and research purposes. In particular, biosensors for a solid-phase fluoroimmunoassay, are becoming an important class of optical biosensor. A technique known as TIRF or total internal reflection, is one method for excitation/detection of fluorescence useful with biosensors for solid-phase assays.

In a typical such apparatus the biosensor is an optical substrate such as a fiber optic rod, to which is adsorbed or covalently bound a binding agent specific for a desired analyte. When the sensor is irradiated with light of an appropriate wavelength, the binding of the analyte to the immobilized binding agent results in a change (either a decrease or increase) in fluorescent emission of a tracer substance. The tracer substance may be the binding agent, the analyte, the complex, or a third, added tracer molecule.

It is desirable to have a system in which the desired sensitivity is achieved without requiring a "wash" step to remove unbound tracer before the fluorescence is measured. One approach to such a system has been to utilize evanescent light to selectively excite tracer molecules directly or indirectly bound to the immobilized binding agent. Evanescent light is light produced when a light beam traveling in a waveguide is totally internally reflected at the interface between the waveguide and a surrounding medium having a lower refractive index. A portion of the internally reflected light penetrates into the surrounding medium and constitutes the evanescent light field. The intensity of evanescent light drops off exponentially with distance from the waveguide surface.

In fluorescence assays using evanescent light, the waveguide is usually glass or a similar silica-based material, and the surrounding medium is an aqueous solution. The region of effective excitation by evanescent light in that situation is generally from about 1000 to about 2000 Å (angstroms). This region is sufficient to include most of the tracer molecules bound to the waveguide surface by means of interaction between the capture molecules and the analyte. However, the bulk of the unbound tracer molecules remaining in solution, will be outside the range of effective excitation and thus will not be stimulated to emit fluorescence.

Desirably, an immunofluorescent biosensor should be capable of detecting analyte molecules at concentrations of $10^{-12}$ or below. To date, most reports of evanescent-type biosensors indicate that at best, concentrations of $10^{-11}$ could be detected.

It is further desirable for speed and convenience in "routine" testing, for example testing of blood bank samples for viral antibodies, to have an evanescent immunofluroescent biosensor which is disposable and which provides multi-sample measurement capability. Multi-sample capability would allow a test sample and a control sample (such as a blank, or, for a competition-type assay, a sample preloaded with tracer molecules) to be simultaneously illuminated and measured. Simultaneous multi-sample capability would also speed up the process of analyzing multiple samples and would reduce the effects of variation in the level of exciting light which are known to occur with typical light sources. However, in a typical prior art evanescent light device such as that of Block et al, U.S. Pat. No. 4,447,546, the waveguide is a fiber optic rod whose shape makes it difficult to build a multi-well biosensor.

Another factor which affects the attainable sensitivity relates to the intensity of excitation light emitted from the waveguide. The intensity of fluorescence emitted by tracer molecules is in part dependent on the intensity of exciting light (which is the evanescent field). Therefore, increased evanescent light intensity should provide increased fluorescence which in turn would improve the detection sensitivity. The level of evanescent light is in turn dependent on the intensity of the light beam propagating in the waveguide and on the efficiency of reflection of light at the interface between the waveguide and the surrounding medium. The typical rod-shaped waveguides are not as effective in internal reflection as a design having two parallel surfaces would be.

Previous methods of immobilizing antibodies to optical substrates in evanescent biosensors also present some problems causing reduction in sensitivity. Many such methods utilize the ε-amino groups of lysine residues in the protein. This approach has at least two significant disadvantages due to the fact that most proteins have multiple lysine residues. First, the presence of multiple potential coupling sites (multiple lysine residues) results in multiple random orientations of antibodies on the substrate surface. If the substrate-coupled lysine residue is near the N-terminal of the antibody molecule, the antibody's antigen binding site (which is near the N-terminal) may be effectively unavailable for binding of the analyte.

Second, if multiple lysines on the same antibody molecule are coupled to the substrate, the molecule may be subjected to conformational strains which distort the antigen binding site and alter its binding efficiency. For capture molecules immobilized by typical prior methods, generally only 20% or less of the binding sites are functional for analyte binding. Thus, it is desirable to have a site-specific method for coupling of the antibodies or other proteins, so that the capture molecules will be uniformly oriented and available for analyte binding.

Another problem relates to the levels of non-specific binding to the antibody-coated surface of the optical substrate. These levels are often sufficiently high to make detection of analyte at concentrations below about $10^{-10}$ molar (abbreviated M) very difficult. Non-specific binding can be reduced by including a wash step after the sample is incubated with the coated substrate, to remove unbound tracer molecules. However, this is time-consuming and complicates the assay procedure. For convenience, a one-shot or homogeneous assay, that is, one which does not require a wash step, is much to be preferred. Second, non-specific binding can be a serious problem unless the surface is "passivated" with a masking agent such as bovine serum albumin or with a thin coating of hydrophilic polymer such as poly(ethylene glycol) or poly(methacrylate). Without such passivation (which introduces yet another step into the procedure), non-specific binding can be 50% or more of the specific binding. Even with passivated surfaces, nonspecific binding can be sufficient to reduce detection sensitivity and reproducibility.

Thus, a need remains for an evanescent biosensor apparatus with improved sensitivity for detection of analytes at picomolar concentrations and below. A need further remains for an immunofluorescent assay and biosensor with properties of low non-specific binding and having uniformly oriented capture molecules.

SUMMARY OF THE INVENTION

The invention comprises a system including both apparatus and methods for an evanescent-light immunofluorescence assay capable of detecting sub-picomolar concentrations of analytes in solution.

The apparatus includes a biosensor comprising a planar waveguide having a plurality of immobilized capture molecules on at least one surface, the capture molecules being constructed to selectively bind a desired analyte. The waveguide surface forms one wall of at least one sample reservoir for holding a sample solution. A light source is included in the apparatus and operably arranged to focus light into the waveguide, where internal reflection within the waveguide results in the production of an evanescent light field which penetrates into the sample solution. In the assay, the test solution also contains a plurality of tracer molecules constructed to emit fluorescence upon stimulation by the evanescent light. The apparatus further includes detection means for detecting fluorescence emitted by the tracer molecules, which is reflective of the amount of analyte bound to the capture molecules.

In a preferred embodiment, multiple wells or channels are provided on the surface of the waveguide, to permit simultaneous comparison of fluorescence from control and sample solutions.

In another preferred embodiment, a substantial portion of the surrounding edge of the waveguide is coated with a reflective coating to prevent light from escaping through the edge, thereby increasing the intensity of the evanescent field.

In another preferred embodiment, the biosensor has the capture molecules site-specifically immobilized such that the percentage of capture sites available is 50 to 75% or more of the number of immobilized capture molecules. In a further preferred embodiment, the waveguide coatings used to immobilize the capture molecules are selected to be resistant to non-specific protein binding.

The invention includes a method of immobilizing the capture molecules at a selected site on the molecule, so that the immobilized capture molecules are substantially uniformly oriented on the waveguide surface. In the method the waveguide surface is coated with a first coating having selected available reactive groups, and the capture molecules to be immobilized are treated to modify a single moiety on each capture molecule to produce activated capture molecules. The modified moiety is constructed to bind to the reactive groups of the first coating. The coated surface with the activated capture molecules under conditions to cause the modified moiety to couple to the first coating and thereby immobilize the activated capture molecules to the waveguide surface.

In one procedure, the waveguide is coated with avidin, and the capture molecules are conjugated to a biotin moiety which has a very strong affinity for avidin. In another procedure, the waveguide coating is a hydrogel film formed of polymethacryloylhydrazide treated to produce free maleimido groups, and the Fab' capture molecules are oxidized to produce reactive thiol groups which can then be reacted with the maleimido groups. In a third embodiment, a silanized waveguide surface is further coated with polyethylene glycol derivatized with ethylenediamine groups. These groups are then reacted with oxidized Fab' capture molecules.

A particular embodiment of the invention is sandwich-type assay capable of detecting sub-picomolar concentrations of human chorionic gonadotrophin. However, the coupling chemistry and apparatus described are useful for any type of fluoroimmunoassay for which the necessary binding reagents are available, including tests for serum antibodies to selected pathogens.

BRIEF DESCRIPTION OF THE DRAWINGS

FIG. 5A is an elevational view of an alternate embodiment of a multi-channel biosensor;

FIG. 5B is a side view of the biosensor of FIG. 5A;

FIG. 5C is a side view of the biosensor of FIG. 5A in a vertical orientation with a sample solution therein;

FIG. 5D is a cross-sectional view of the biosensor taken along line D—D in FIG. 5C;

FIG. 6 is an elevational view of an alternate embodiment of a multiwell biosensor;

DETAILED DESCRIPTION OF THE ILLUSTRATED EMBODIMENTS

Figure 1:
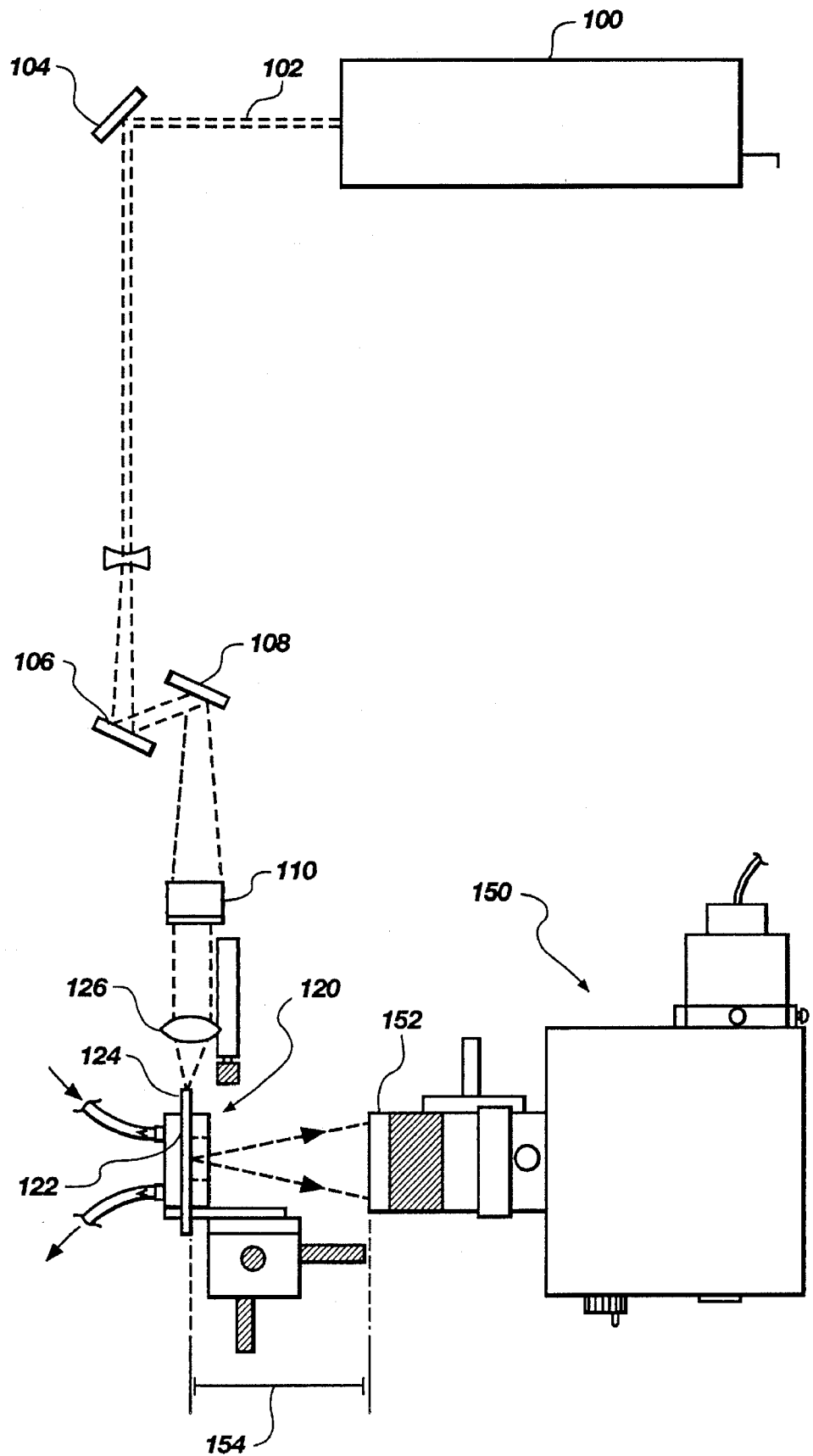
FIG. 1 is a schematic diagram of a fluorescent immunoassay apparatus of the invention.

A light source 100 provides a light beam 102 which is directed by means of mirrors 104, 106, 108 to an optical biosensor indicated generally at 120 (FIG. 1). In the working embodiment, light source 100 is an argon laser capable of emitting light at wavelengths of between about 488 and 514.5 nanometers (abbreviated nm). In an alternate embodiment, a laser diode emitting at wavelengths of 600 to about 700 nm can be used as light source 100. Depending on the requirements of the fluorescent tracer, light source 100 may also be embodied as any other laser or other high-intensity light source emitting a sufficient amount of light at an appropriate wavelength to excite the selected tracer.

The embodiment of FIG. 1 further includes a 45° angle mirror 110 which is positioned for making beam 102 a vertical beam prior to focussing the beam onto the biosensor. It will be understood by those skilled that the number and arrangement of mirrors 104, 106, 108, 110 may be varied as necessary to accommodate various space limitations, with the sole requirement being that a sufficient amount of light be directed to biosensor 120.

Biosensor 120 has an optical substrate 122 with one end 124 positioned to receive light from beam 102. A focussing lens 126 is positioned between angle mirror 110 and end 124 of waveguide 122, for focussing light from beam 102 onto end 124. Desirably, focussing lens 126 is mounted on an X–Y translation unit so that its position may be adjusted for best focussing.

Light detection means indicated generally at 150 are positioned to detect fluorescent light emitted from biosensor 120. The emitted light is reflective of the concentration of a selected analyte in a sample, as is better described subsequently in reference to FIGS. 2 and 7–10. Light detection means 150 includes a collection lens 152 positioned to collect the emitted fluorescence in a direction substantially orthogonal to the direction of propagation of light beam 102 through optical substrate 122.

The distance 154 between collection lens 152 and optical substrate 122 is selected as known to those skilled to maximize the collection of light emitted from the region of evanescent light penetration. The light collected by collection lens 152 is then sent to detection means 150, which responds by outputting signals reflective of the level of collected fluorescence light.

Figure 4A:
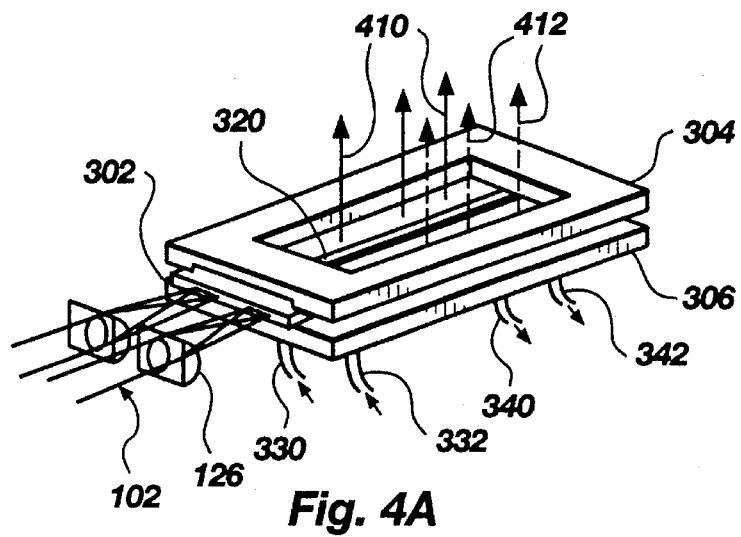
FIG. 4A is an elevational view of a two-channel flow biosensor of FIGS. 3A–3B with respect to exciting light beams and the collection of fluorescence in an immunoassay.
Figure 4B:
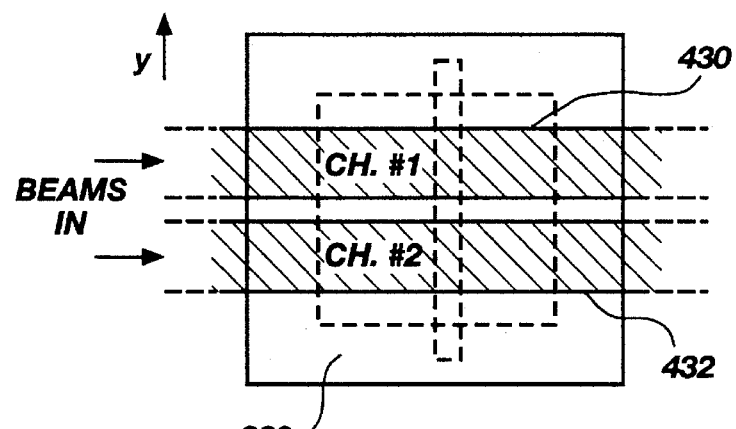
FIG. 4B is a schematic diagram of the two-channel biosensor indicating the arrangement of two types of detection devices, a CCD detector and a spectrometer slit, with respect to the waveguide regions.
Figure 4C:
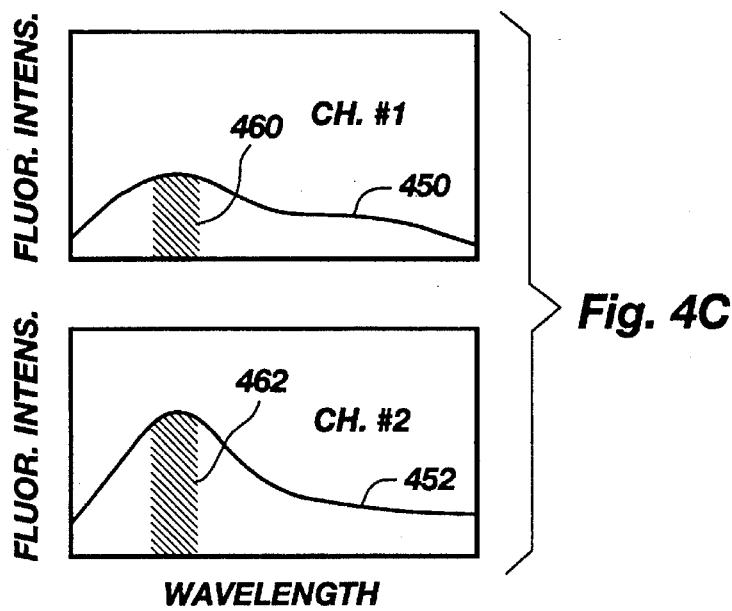
FIG. 4C is a diagram of fluorescence intensities as they might be detected from the two channels of a biosensor arranged according to FIGS. 4A and 4B.

Detection means 150 may be any type of photodetector useful to detect light in the wavelength region spanning the wavelength range of the emitted fluorescence, as known in the art. In FIG. 1, detection means 150 is a CCD (charge-coupled device) detector which produces a signal like that depicted in FIG. 4C. Means are provided to integrate the signal function around each peak to determine the total collected fluorescence from the sample.

Alternatively, detection means 150 may be a photomultiplier, a semiconductor photodiode, or an array of such detectors. In embodiments other than a CCD, an array is generally preferable to a single detector for some purposes. With an array of small detectors, the user can determine that the peak fluorescence is being detected and is not inadvertently missed due to misalignment of the collection and detection optics. However, in an embodiment for routine use such as in a testing laboratory, and for which all the parameters of the assay have been standardized, the spectrograph may be replaced by a filter which passes only wavelengths in the region of tracer fluorescence.

Figure 2:
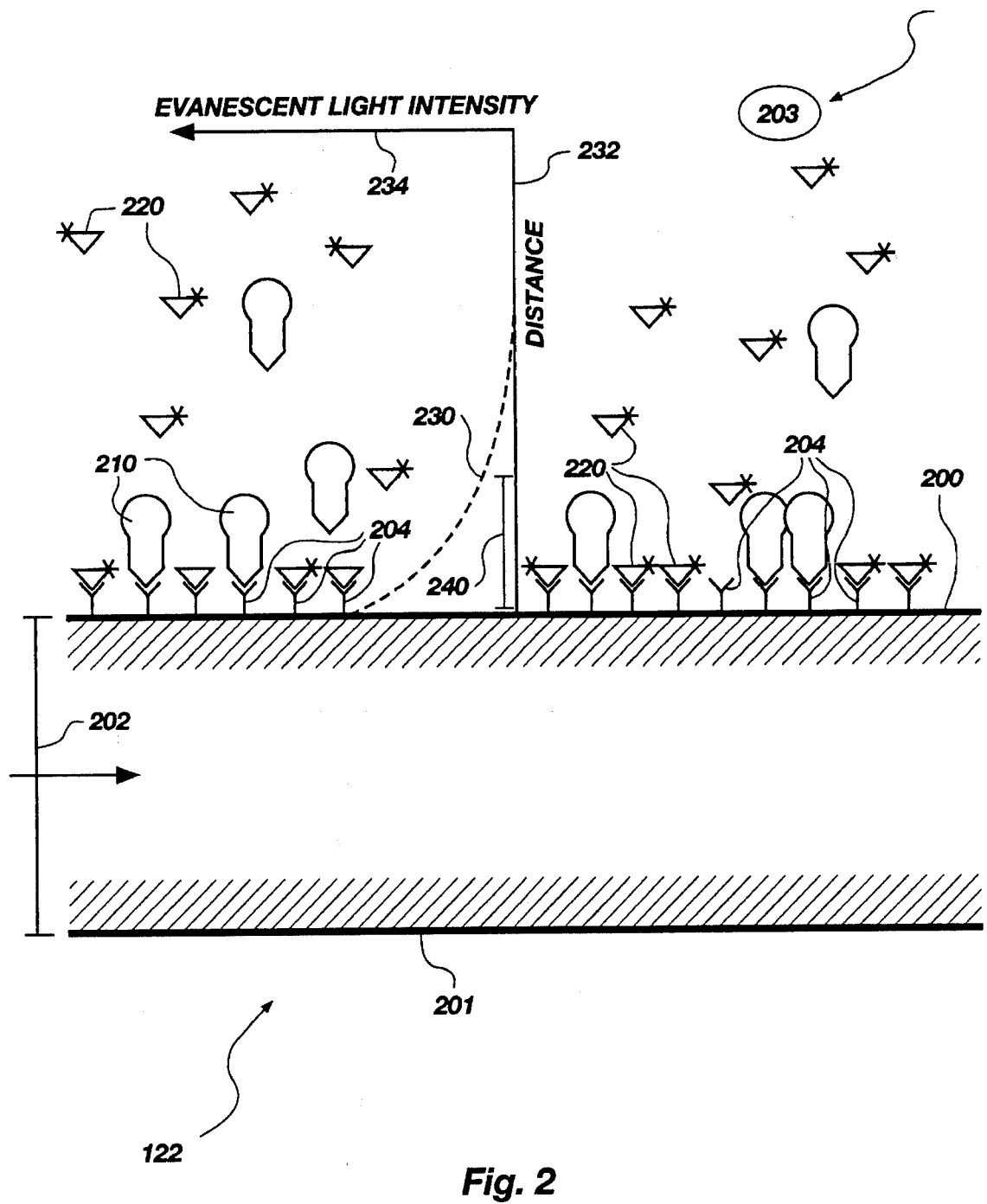
FIG. 2 is a side view of a portion of the waveguide and the biochemical components of a competition immunofluorescent assay according to the invention.

In contrast to the rod-shaped fiber optic waveguides typically found in immunofluorescent assay devices, in the present invention optical substrate 122 is of generally planar shape having two planar surfaces spaced by a width, as shown in FIG. 2. Optical substrate 122 may for example be a square or rectangular glass microscope slide or coverslip, or the like. Materials for optical substrate 122 include glass, high-lead glass, quartz, optical plastic, and the like as are well-known in the art.

Figure 3C:
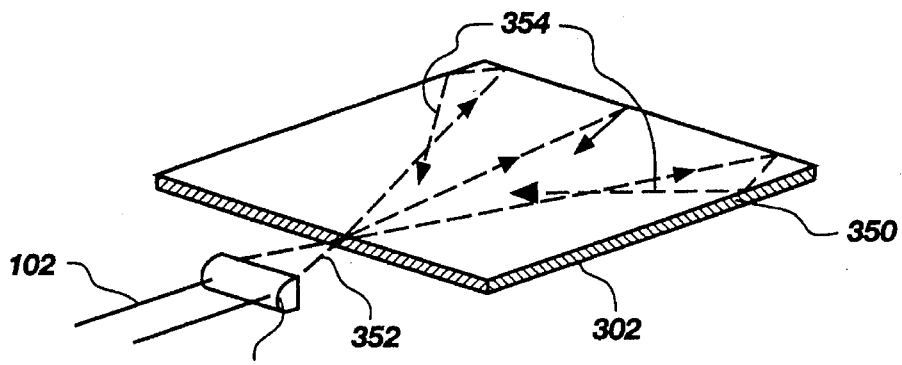
FIG. 3C shows the waveguide in isolation as it could be arranged with respect to a cylindrical lens and incoming and reflected light waves.

For focussing light beam 102 onto the end of the planar substrate waveguide, it is preferred to replace the typical spherical lens with a lens of approximately half-cylindrical shape, as better seen in FIGS. 3C and 5A. The curved side of the lens need not be a strict half cylinder, but may have an ellipsoidal profile.

As is better seen in FIG. 2, optical substrate 122 is embodied as a planar waveguide having at least one planar surface 200 spaced from a second surface 201 by a width 202. At least surface 201 is disposed in contact with a sample solution 203. A plurality of capture molecules 204 are immobilized on surface 201. The sample solution contains a plurality of analyte molecules 210 of a selected analyte, and a plurality of tracer molecules 220. The capture molecules are chosen or constructed to bind to a binding moiety present on each of the analyte molecules 210. The tracer molecule 220 is chosen or constructed to emit fluorescent light in response to stimulation by light of the appropriate wavelength. The level of fluorescence emitted by the tracer molecules 220 is a measure of the amount of analyte bound to the capture molecule and is thereby reflective of the concentration of analyte molecules 210 in the solution.

When light is being propagated in the waveguide 124 and internally reflected at the surfaces 200, 201, an evanescent light field is produced having an intensity curve 230 which drops off with distance from the surface 200, as diagrammed relative to a distance axis 232 and an intensity axis 234 (not to scale). It will be apparent that an excitation zone 240 is the only region of the solution in which the evanescent light intensity is sufficient to excite a significant or detectable fraction of tracer molecules 220 (not to scale). Tracer molecules 220 which are outside this zone will contribute little or no induced fluorescence. Excitation zone 240 is typically between about 1000 and 2000 Å in width.

Capture molecules 204 may be whole antibodies, antibody fragments such as Fab' fragments, whole antigenic molecules or antigenic fragments, and oligopeptides which are antigenic and/or similar in 3-dimensional conformation to an antibody-binding epitope.

In FIG. 2, a competition assay scheme is depicted (also termed a displacement assay). However, with appropriate modifications to the assay scheme which will be apparent to the skilled person, alternate assay schemes such as sandwich assays may be performed with the present apparatus.

The capture molecules 204 may be immobilized on the surface 202 by any method known in the art. However, in the preferred embodiment the capture molecules are immobilized in a site-specific manner. As used in this application, the term "site-specific" means that specific sites on the capture molecules are involved in the coupling to the waveguide, rather than random sites as with typical prior art methods. Examples I–III detail methods for site-specific immobilization of capture molecules to the surface of the optical substrate by means of a protein-resistant coating on the substrate.

As previously stated, the intensity of evanescent light drops off rapidly with distance from the waveguide surface. Thus, only tracer molecules which are within an effective excitation range 240 (not necessarily to scale) from the waveguide surface, will be excited by the evanescent light to emit fluorescence. The range 240 is generally about 1000 to 2000 Å. This range is sufficient to ensure that essentially all tracer molecules 220 which are bound (directly or indirectly) to capture molecules 204, will be detected, while the bulk of the tracer molecules which remain free in solution are outside the effective excitation range.

In a working embodiment of the apparatus of FIG. 1, measurements of fluorescence are made by spectroscopy. For the examples involving rhodamine-tagged molecules, light source 100 is an argon ion laser (a LEXEL Model 95-2) at an emission wavelength of 514 nm. Fluorescence detection was done with a monochromator (SPEX Industries, Inc., Model 1680C) and a charge-coupled device (abbreviated CCD) (Photometrics Ltd. Series 200). Alternatively, light source 100 can be any laser emitting at the wavelength desired for excitation of selected fluorescent dyes. Also, once an assay procedure has been validated and standardized, it may not be necessary to measure the fluorescence spectrum or spatial distribution of fluorescence. The detection means may be simplified in accordance with the minimum requirements of the assay.

In another alternate embodiment, light source 100 is a laser diode emitting in the red wavelength region of 600–700 nm, available from Hitachi. This laser diode provides about 5 milliwatts of power with a peak emission wavelength of about 670 nm. For an embodiment using a laser diode, it is necessary to use dyes such as cyanine dyes, whose fluorescence can be stimulated by excitation with wavelengths in the red spectral region. An example of such a dye is CY5, available from Biological Detection Systems, Inc., Pittsburgh, Pa. (catalog no. A25000). The CY5 dye can be conjugated to the desired tracer molecule by the manufacturer's instructions and/or with a kit available from BDS. The dyes and methods for conjugating are characterized in the paper by Southwick, P. L., et al., titled "Cyanine Dye Labelling Reagents—Carboxymethylindo-cyanine Succinimidyl Esters", *Cytometry* 11:418–430 (1990).

In the experiments described herein and whose results are shown in FIGS. 7–10, data acquisition and processing was accomplished using software supplied with the Photometrics Series 200.

In the embodiment of FIG. 2, the immunoassay is a competition assay in which the tracer molecules 220 are constructed such that capture molecules 204 will bind tracer molecules 220 in place of analyte molecules 210. Higher concentrations of analyte molecules 210 will cause most of the tracer molecules 220 to be displaced into the surrounding solution from capture molecules 204, thus reducing the number of tracer molecules within excitation range 240 of the substrate 122. This reduced binding of tracer molecules in turn reduces the amount of fluorescence. In contrast, lower concentrations of analyte molecules 210 will allow tracer molecules 220 to bind to capture molecules 204, and thus to be held within the excitation range 240.

Figure 3B:
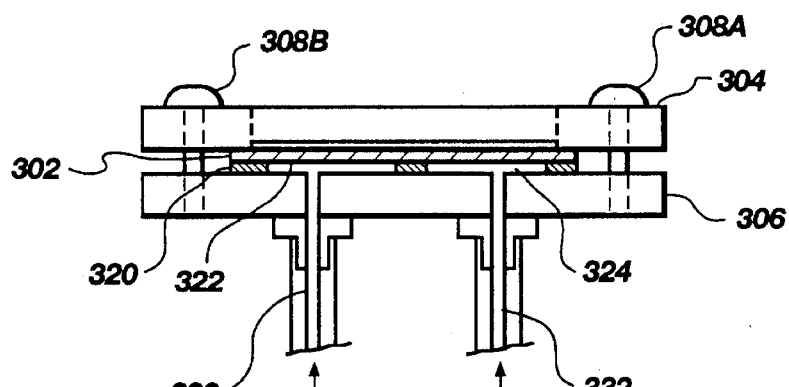
FIG. 3B is a side cross-section view of the flow biosensor taken along line B—B in FIG. 3A.
Figure 3A:
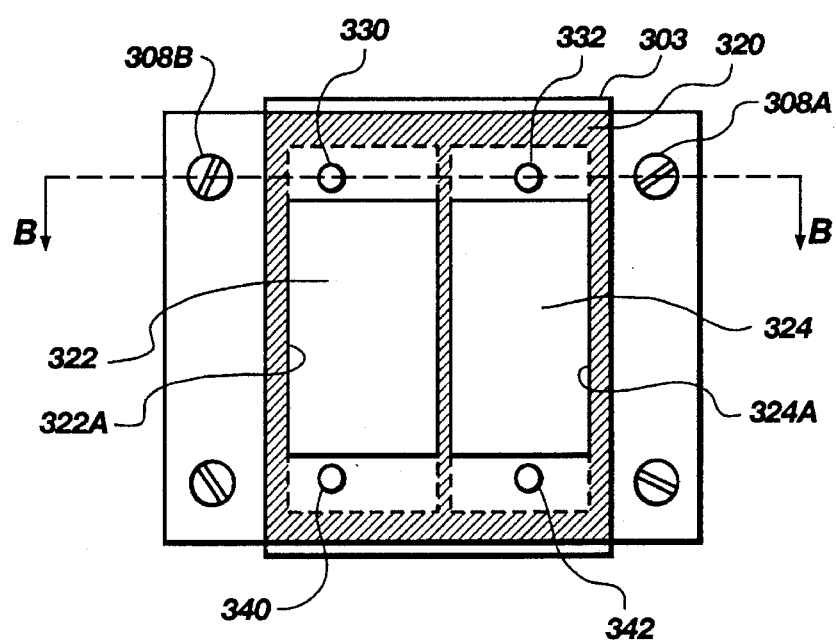
FIG. 3A is a top view of a flow biosensor of the apparatus of FIG. 1.

In the embodiment of FIG. 1, biosensor 120 is shown as a flow-through cell, shown in greater detail in FIGS. 3A–B. A planar waveguide 302 which may be for example a microscope slide or coverslip, is sandwiched between two plates 304, 306 which are held together by screw fittings 308A, 308B. A gasket 320 is seated between waveguide 302 and plate 306. Gasket 320 is configured with two internal openings which, when gasket 320 is securely sandwiched between plate 306 and waveguide 302, form reservoirs 322, 324. In reservoirs 322, 324, waveguide 302 constitutes one wall, plate 306 constitutes a second wall, and the inner edges 322A, 324A of the gasket form the remaining walls. Although the reservoirs 322, 324 are here shown to be rectangular in shape, other shapes could be used. Also, instead of two reservoirs as depicted in FIG. 3A, the gasket could have either just one opening or more than two, creating corresponding numbers of individual reservoirs.

Gasket 320 is preferably made of a semi-rigid material having an index of refraction less than that of the waveguide material in the wavelength range of the exciting light. For best results, it is believed that the index of refraction of the gasket material should be as low as possible compared to that of the waveguide. For a waveguide made of quartz or glass would typically be about 1.5, higher for high-lead glass. A transparent (non-pigmented) silicon rubber (siloxane polymer) with an index of refraction of 1.35–1.4 is a presently preferred material for gasket 320. TEFLON materials such as FEP or TEF (polytetrafluoroethylene and —) often have indices of refraction of around 1.4–1.45, and may also be suitable. However, because TEFLON surfaces tend to adsorb protein in a non-specific manner, silicon rubber is generally preferred. The Teflon-type materials, FEP or TEF, are also acceptable.

The lower plate 306 in FIG. 3B, has a pair of inlets 330, 332 and a pair of outlets 340, 342. These inlets and outlets are arranged so as to permit solutions to flow separately through the respective reservoirs 322, 324. Desirably, the lower plate 306 may be made from aluminum alloy.

FIG. 3C shows the waveguide 302 in isolation from the remaining parts of the biosensor. Lens 126 is shown receiving and focussing light beam 102 onto the waveguide. Desirably, the outer, surrounding edge 350 is coated with a reflective material, except for an uncoated region 352 at which the focussed light from lens 126 enters the waveguide (FIG. 3C). Arrows 354 indicate reflection from the coated edges. In FIG. 3C, only one lens and one uncoated region are shown, however, for two or more channels, more portions of edge 350 may be left uncoated to allow light to enter the waveguide (see for example FIG. 4A).

The reflective coating reflects back into the waveguide, light that would otherwise escape through the edge 303. The intensity of the evanescent light wave is thereby enhanced. Suitable reflective coating materials include aluminum, silver, or the like, as known in the art. Alternatively, in place of a coating, reflectors could be positioned about the edges to reflect escaping light back into the waveguide.

The design with at least two individual reservoirs has significant advantages over a single reservoir embodiment for instances in which it is desirable to measure the test sample fluorescence simultaneously with fluorescence from a control region on the same waveguide. For example, the level of non-specific binding to the waveguide can be subtracted from the test sample fluorescence. Also, measurement changes due to fluctuations in intensity of the exciting light can be corrected for. In a displacement assay, the "control" region could be the preloaded waveguide with no analyte present in the sample, or with a known amount of analyte.

FIGS. 5A–5D depict an alternate embodiment of a biosensor useful with the apparatus of FIG. 1. The biosensor indicated generally at 500 has an integrally mounted or formed focussing lens 502 and waveguide 504 arranged such that lens 502 focusses light onto the forward end 506 of the waveguide. Focussing lens 502 is configured and positioned to focus a light beam onto the receiving end 506 of the waveguide 504 (FIGS. 5A, 5C). Side walls 511, 512, top and bottom walls 516, 517, and a removably sealing rear wall 518 enclose the space about the waveguide 504 to create reservoirs 520, 522.

The integral focussing lens 502 replaces focussing lens 126 in the apparatus of FIG. 1. In the working embodiment of FIGS. 5A–5D, the focussing lens is molded as part of the waveguide holder 500 of an optical plastic such as polystyrene, polycarbonate or the like.

Biosensor 500 also includes reservoirs 520, 522 best seen in FIGS. 5B, 5C and 5D in which sample solutions can be disposed. Optionally, for some applications it may be desirable to provide lengthwise ribs 530 (FIG. 5D) along slot 504 which can define separate regions of the waveguide surface.

FIG. 6 depicts an alternate multiwell biosensor similar to that of FIGS. 5A–5C, except that a series of discrete wells 600, 602, 604, 606 are formed on the waveguide 504. The embodiment of FIG. 6 would be used in a horizontal position, so that the wells 600, 602, 604, 606 need not be covered.

The biosensor including the lens may be formed by molding of a suitable optical plastic. The holder may be pre-molded, and a silica-surface waveguide inserted subsequently with a refractive-index-matched adhesive to secure it in place and seal it as needed to create separate channels. Alternatively, the waveguide holder may be molded with a silica-surface waveguide in place, thereby eliminating the need for the adhesive.

In still another embodiment, the waveguide could itself be formed of the optical plastic and molded simultaneously with the holder. The latter type construction is not suitable for use with excitation wavelengths of 488 to 515 nm, because known optical plastics tend to emit fluorescence in this (the blue) wavelength region. However, an alternate embodiment of the apparatus using a laser diode as the light source emitting at wavelengths of 600 nm and above, would accommodate a plastic waveguide.

The following examples detail three methods for attaching the capture molecules to the waveguide surface in a site-specific manner. The general scheme for reducing the level of non-specific binding is to coat the waveguide with a protein-resistant material, and then immobilize the antibody to the coating. The scheme further includes derivatizing the protein-resistant coating combined with site-specific modification of the antibody or other capture molecule to be immobilized, so as to provide site-specific attachment of the capture molecule to the coating. Of the three examples presented, the procedures of Examples I and II gave generally better results. At present, the avidin-biotin coupling method (Example II) is the most preferred. Using either coupling scheme, at least about 75% of the immobilized Fab' fragments were active, and the levels of non-specific binding were typically no more than 1–2% of the specific binding. The modified PEG coating gave slightly higher levels of non-specific binding, in the range of 5% to about 25%.

EXAMPLE I

Preparation of Waveguide Surface—Hydrogel

A silica surface was prepared with a hydrogel coating comprised of polymethacryloyl hydrazide (abbreviated PMahy). Fused silica slides of CO grade and thickness about 1 mm, available from ESCO, Inc., were suitable as waveguides (optical substrates).

To graft the PMahy to the silica, the surface was derivatized with aldehyde groups. The derivatization was accomplished by silanization with 3-aminopropyltriethoxy silane (abbreviated APS) to add an amino functional group, followed by reaction with glutaraldehyde to produce free aldehyde groups. The PMahy was then be reacted with these aldehyde groups to form the hydrogel coating.

Antibodies could be coupled to this hydrogel in at least two ways. In one method, the carbohydrate groups in the Fc antibody region are oxidized to aldehydes by treatment with sodium metaperiodate. However, few antigen-binding fragments contain carbohydrate moieties useful for this purpose. Thus, a preferred method comprised modifying the pendant hydrazido groups of the hydrogel to a maleimido group by treatment with succinimidyl 4-(N-maleimido-methyl)cyclohexane-1-carboxylate (abbreviated SMCC; Pierce Chemicals). These maleimido groups can be reacted with the free thiol groups typically found in the C-terminal region of Fab' fragments, thereby coupling the Fab' fragments to the hydrogel.

Polymethacryloylchloride (abbreviated PMaCl) was prepared by radical polymerization of methacryloyl chloride (abbreviated MaCl) in dioxane under an inert atmosphere, as described in Jantas et al., *J. Polym. Sci., Part A: Polym. Chem.* 27:475–485 (1989).

A reaction mixture containing 21.1. mole % of MaCl, 78.1 mole % dioxane, and 0.8 mole % AIBN (azobisisobutyronitrile), was allowed to react for 24 hours at 60° C. with agitation. The PMaCl so produced remained in solution during the course of the reaction. The mixture was then diluted with twice the amount of dioxane used in the reaction and slowly added to an excess of hydrazine hydrate, to achieve a volumetric ratio of 2:5 for diluted PMaCl. The latter addition was carried out for about 30 minutes in an ice bath under a nitrogen atmosphere. The resulting mixture was then stirred for about an hour at room temperature. The product PMahy was purified by evaporation of dioxane and the remaining unreacted hydrazine hydrate, followed by washing in distilled water. The washed product was then dialyzed in a SpectraPor dialysis membrane having a molecular weight cut-off of 3,500 daltons, to remove unreacted monomer.

The polymer so prepared was shown to have a molecular weight of about 26,000 as measured by gel permeation chromatography for the hydrochloride form. The concentration of polymer in solution in the hydrochloride form was estimated to vary between about 5% and 8% (w/v). It has been found that the polymer can be stored in aqueous solution at 4° C. under a nitrogen atmosphere, for at least 5 months without undergoing a detrimental amount of spontaneous cross-linking.

Silica chips or glass or quartz microscope slides were cleaned with chromic acid, then treated with 5% APS/95% deionized water (v/v) for about fifteen minutes at room temperature. The APS-treated surfaces were rinsed with deoionized water and absolute ethanol, and incubated in a vacuum oven which had been flushed at least three times with nitrogen, at 120° C. for 1 hour. The resulting silanized surfaces were then soaked in 2.5% glutaraldehyde (E.M. grade from Polysciences) in 0.1M carbonate-bicarbonate buffer, pH 9.2, for two hours at room temperature.

Next, linear PMahy was reacted with the aldehyde groups on the treated chips to create a cross-linked polymer film with many unreacted hydrazido groups in the chains. This was done by dipping the treated chips in solutions of PMahy of between about 5% and 8% (w/v), pH 5.2, at a temperature between about room temperature and about 60° C., for a time sufficient to form a polymer film of thickness about 100 Å or less. The thickness of the hydrogel layer increases with time and temperature of incubation in the solution. It was found that optimal conditions for preparation of the film of 100 Å thickness or less, comprised incubating in 5% (w/v) PMahy for 2 hours at room temperature (about 25° C.).

Next, the free hydrazido groups of the polymer film were modified by treatment with SMCC to provide reactive maleimido groups on the ends of the polymer side chains. This was done by immersing the PMahy-coated substrates in a solution of 0.19% (w/v) SMCC in dimethylformamide for about 1 hour at 25° C.

Following derivatization with SMCC, the hydrogel-coated surfaces were treated with a 1 mg/ml solution of Fab' fragments in phosphate buffer, ph 6.0, with 5 mM EDTA. The waveguide surface so prepared was shown to immobilize IgG molecules at a surface density of about $1.4 \times 10^{-12}$ moles/cm$^2$. Also the surface was able to immobilize Fab' fragments at their C-terminal thiol groups in a site-specific way. The thickness of the resulting polymer film was determined by ellipsometry to be about 100 Å, as was desired. This film thickness is much less than typical previous polymeric films, which have thicknesses of 0.35 to 25 μm (microns). The above-described method of preparing the PMahy polymers is superior to that described by von Kern et al. using polymethacryloylacid esters. Such esters suitable for reaction with hydrazine hydrate often have a molecular weight of 80,000 daltons or more, from which it is difficult to obtain a desirably thin film on the waveguide.

Finally, the Fab' fragments were coupled to the free maleimido groups pendant from the polymer-coated surface as follows. The prepared waveguide surface was incubated for 24 hours at 4° C. in a solution containing the Fab' fragments at a concentration of $1.5 \times 10^7$ molar, in a phosphate buffer with 5 mM EDTA (pH 6.0).

EXAMPLE II

Preparation of Waveguide Surface—Avidin-Biotin

This strategy was designed to exploit the very strong binding affinity of biotin for avidin (binding constant of around $10^{-15}$). An avidin coating was readily made by physical adsorption on a silica surface. The Fab' fragments were then conjugated with biotin to form biotin-Fab' conjugates, also referred to as biotinylated Fab' fragments or b-Fab' fragments. The biotin is coupled at specific location(s) on the Fab' fragments. The avidin coated surface is then treated with the b-Fab' fragments, so that the biotin binds to the avidin thereby immobilizing the Fab' fragment to the surface in a site-specific manner.

In actual experiments, the procedure was as follows. Chromic acid-cleaned silica surfaces were immersed in a solution of $3 \times 10^{-6}$M (molar) avidin for about 3 hours at room temperature. The surfaces were then washed several times in PBS to remove unadsorbed avidin.

Biotinylated Fab' conjugates were prepared from a solution of Fab' fragments in PBS (0.5–1 mg/ml), by addition of a sufficient amount of 4 mM biotin-HPDP in dimethylformamide to provide a 20-fold molar excess of biotin-HPDP. This mixture was incubated for 90 minutes at room temperature, and biotinylated Fab' fragments (abbreviated b-Fab') were purified by gel permeation chromatography with Sephadex G25 equilibrated in PBS.

An alternate method was used for biotinylating whole antibodies, in which biotin-LC-hydrazide was coupled to oxidized carbohydrate groups in the Fc region of the antibody. Mab designated 9-40 (a murine monoclonal IgG$_1$ antibody that binds fluorescein), was oxidized by incubation at a concentration of 1–2 mg/ml protein in 10 mM sodium periodate, 0.1M sodium acetate pH 5.5 for 20 minutes at about 0° C. Glycerol was then added to a final concentration of 15 mM to quench the reaction, and the mixture incubated a further 5 minutes at 0° C. The oxidized Mab 9-40 was purified by gel filtration chromatography on Sephadex G25 equilibrated with 0.1M sodium acetate buffer pH 5.5, and then reacted with 5 mM biotin-LC-hydrazide for 2 hours at room temperature with agitation. Unreacted biotin-LC-hydrazide was removed using a Sephadex G25 column equilibrated in PBS.

Avidin-coated surfaces were immersed in a $1.5 \times 10^{-7}$M solution of b-Fab' fragments for about an hour at room temperature, followed by washing with PBS to remove unbound b-Fab' fragments. Optionally, polyethylene glycol (abbreviated PEG) was coupled to surfaces that were previously coated with the b-Fab' fragments, by immersion of the b-Fab'-coated surfaces in a solution of between about $5 \times 10^{-8}$ and $1 \times 10^{-7}$M PEG. Unbound PEG was removed by washing in PBS.

EXAMPLE III

Preparation of Waveguide Surface—PEG-Type

In this method, the terminal hydroxyl groups of polyethylene glycol (abbreviated PEG) were converted to primary amine or hydrazide groups by reaction with ethylenediamine (abbreviated ED) or hydrazine, respectively. The PEG molecules so modified were then coupled to APS-glutaraldehyde activated silica surfaces.

Monofunctional (PEG M2000, M5000) or difunctional (PEG 3400, PEG 8000, PEG 18,500) of the indicated molecular weights in daltons, were reacted with p-nitrophenyl chloroformate (abbreviated p-NPC; obtained from Aldrich Chemicals) in solution in benzene. The mixture was agitated at room temperature for about 24 hours. Dry ethyl ether (less than 0.01% water, purchased from J.T. Baker Chemicals) was used to precipitate PEG-(o-NP)$_2$ from solution. The precipitate was vacuum-dried overnight. Between about 50% and about 100% of PEG molecules were converted by this treatment to PEG-Onp, as determined by hydrolysis with 0.1N sodium hydroxide to release the p-nitrophenol groups. The absorbance at 402 nm was determined spectrophotometrically and a molar extinction coefficient of $18400 M^{-1} cm^{-1}$ used to determine the amount of conversion. The level of conversion depended somewhat on the molecular weight of the PEG of MPEG.

PEG-(o-NP)$_2$ was then dissolved in ethylenediamine and agitated gently for about 3 hours at room temperature. The PEG-(ED)$_2$ was then precipitated by addition of a sufficient amount of dry ethyl ether. The yellow PEG-(ED)$_2$ solution was decolorized by addition of 1 drop of 12N (normal) hydrochloric acid, and the precipitation with ethyl ether repeated twice more. The wet PEG-(ED)$_2$ was dried under vacuum overnight. Alternatively, in place of ethylenediamine, the PEG was derivatized with hydrazine to produce PEG-Hz$_2$.

The modified PEG was coupled to silanized-glutaraldehyde-treated waveguide surfaces prepared as described in Example I. A solution of 24 milligrams (mg) of PEG-ED powder dissolved in 1.2 milliliters (ml) of 0.15M PBS pH 7.4 or in the same volume of 11% potassium sulfate-sodium acetate buffer at pH 5.2. The prepared waveguide surfaces were immersed in the PEG-ED solution and incubated at 60° C. for about 24 hours. The procedure using K$_2$SO$_4$-acetate buffer yielded a higher density of PEG molecules attached to the surface than that using PBS buffer.

| | | | Summary of Solid-Phase Immunoassays using Silica Substrates | | | | |
|---|---|---|---|---|---|---|---|
| Surface[1] | Antibody[2] | Coupling Chemistry | Total Binding[3] ($\times 10^{-12}$) (moles/cm$^2$) | Absolute Non-specific Binding[4] ($\times 10^{-12}$) (moles/cm$^2$) | Relative Non-specific Binding (%) | Immobilized Antibody[5] ($\times 10^{-12}$) (moles/cm$^2$) | Specific Activity[6] (%) |
| Hydrophobic Silica (DDS) | Heat Treated IgG | Random | 0.65 | 0.04 | 6.46 | 3.00 | 21.67 |
| Hydrophobic Silica (DDS) | Acid Treated IgG | Random | 0.67 | 0.07 | 9.70 | 2.20 | 30.45 |
| Hydrophobic Silica (DDS) | Fab' Fragment | Random | 0.37 | 0.25 | 69.00 | 1.30 | 28.46 |
| Silica/APS/GLU | Acid Treated IgG | Random | 0.55 | 0.21 | 38.18 | 3.75 | 14.67 |
| Silica/APS/GLU/PEG | Oxidized IgG | Specific | 0.56 | 0.11 | 19.64 | 2.06 | 27.18 |
| Silica/APS/GLU/PEG | Oxidized IgG | Random | 0.41 | 0.10 | 24.39 | 1.44 | 28.47 |
| Silica/Avidin | Biotin-IgG | Specific | 0.72 | 0.02 | 2.92 | 0.94 | 76.60 |
| Silica/Avidin | Biotin-Fab | Specific | 0.84 | 0.02 | 2.62 | 1.10 | 76.36 |
| Silica/Avidin (with biotin-PEG) | Biotin-Fab | Specific | 0.80 | 0.02 | 1.88 | 1.10 | 72.73 |
| Silica/Hydrogel (preswollen) | Oxidized IgG | Specific | 0.17 | 0.01 | 6.88 | 7.95 | 2.14 |
| Silica/Hydrogel (preswollen) | Fab' Fragment | Specific | 1.51 | 0.03 | 2.03 | 2.76 | 54.71 |

[1]Abbreviations: DDS — dichlorodimethylsilane; APS — aminopropysilane, GLU — glutaraldehyde; PEG — polyethylene glycol (3400 MW); BSA — bovine serum albumin; IgG — intact immunoglobulin G; Fab' — antigen binding fragment with reactive thiol group; ND — not determined
[2]All immunoassays were performed with an IgG, monoclonal antibody (9-40) which binds fluorescein.
[3]Amount of $^{125}$I-Fluorescein-BSA which bound to silica substrate.
[4]Amount of $^{125}$I-BS4 which bound to silica substrate.
[5]Amount of $^{125}$I-9-40 immobilized on silica substrate.
[6]Percent of immobilized active sites which bound antigen molecules.

TABLE II

| | | Summary of Solid Phase Immunoassays Using Silica Substrates Covered with Hydrogel with Maleimido Reactive Groups | | | | | | |
|---|---|---|---|---|---|---|---|---|
| Antibody | Binding Constant pK$_0$ | Immobilized Antibody ($\times 10^{-12}$ mol/cm$^2$) | Total hCG Binding in 5 min ($\times 10^{-12}$ mol/cm$^2$) | Total hCG Binding in 60 min ($\times 10^{-12}$ mol/cm$^2$) | Antibody Activity (%) | Absolute Non-specific Binding in 5 min (BSA) ($\times 10^{-12}$ mol/cm$^2$) | Relative Non-specific Binding in 5 min (BSA) (%) | Absolute Non-specific Binding in 60 min (BSA) ($\times 10^{-12}$ mol/cm$^2$) | Relative Non-specific Binding in 60 min (BSA) (%) |
| Fab' from Anti-hCG-A | 8.85 | 1.39 ± 0.07 | 0.62 ± 0.03 | 0.81 ± 0.03 | 58.3 ± 0.8 | <0.01 | <0.97 | <0.02 | <2.47 |
| Fab' from Anti-hCG-B | 7.89 | 1.29 ± 0.06 | 0.51 ± 0.02 | 0.67 ± 0.03 | 51.9 ± 0.1 | 0.02 ± 0.01 | 3.85 ± 1.81 | 0.04 ± 0.01 | 5.91 ± 1.22 |
| Fab' from Anti-hCG-C | 8.70 | 0.74 ± 0.04 | 0.18 ± 0.01 | 0.41 ± 0.02 | 55.4 ± 0.3 | <0.01 | <6.22 | 0.03 ± 0.01 | 7.21 ± 2.09 |
| Fab' from Anti-hCG-D | 8.00 | 1.45 ± 0.06 | 0.58 ± 0.02 | 0.75 ± 0.03 | 51.4 ± 0.3 | <0.01 | <1.20 | <0.02 | <3.21 |
| Fab' from Mouse IgG | — | 2.50 ± 0.10 | 0.04 ± 0.01 | 0.06 ± 0.02 | 2.4 ± 0.7 | — | — | — | — |

TABLE III

Summary of Solid Phase Immunoassay Using Silica Substrates with Adsorbed Avidin and Biotinylated Fab' Fragmebts

| Antibody | Immobilized Antibody ($\times 10^{-12}$ mol/cm$^2$) | Total hCG Binding ($\times 10^{-12}$ mol/cm$^2$) | Specific Activity (%) | Absolute Non-specific Binding (BSA) ($\times 10^{-12}$ mol/cm$^2$) | Relative Non-specific Binding (BSA) (%) |
|---|---|---|---|---|---|
| Fab' from Anti-hCG-A | 1.19 ± 0.02 | 1.22 ± 0.01 | 100 ± 5 | 0.05 ± 0.02 | 4.20 ± 0.02 |
| Fab' from Anti-hCG-B | 1.40 ± 0.05 | 1.38 ± 0.07 | 98 ± 9 | 0.05 ± 0.01 | 3.57 ± 0.02 |
| Fab' from Anti-hCG-C | 2.24 ± 0.02 | 1.10 ± 0.03 | 49 ± 3 | 0.05 ± 0.02 | 2.32 ± 0.01 |
| Fab' from Anti-hCG-D | 1.59 ± 0.02 | 1.24 ± 0.01 | 78 ± 2 | 0.05 ± 0.005 | 3.14 ± 0.01 |
| Fab' from Mouse IgG | 1.25 ± 0.02 | 0.03 ± 0.003 | 2.4 ± 0.05 | 0.09 ± 0.03 | 7.20 ± 0.03 |

Antibodies or other binding proteins were immobilized to the PEG-coated waveguides as follows. A solution of about 3 mg/ml of antibody was dissolved in 0.15M sodium acetate buffer, pH 5.2. A solution of equivalent weight of 50 mM sodium metaperiodate (NaIO$_4$) was then added, and the reactants were agitated at room temperature for about an hour. Unreacted sodium metaperiodate was removed by passing the reaction mixture through a desalting column (type PD-10 from Pharmacia), which had been pre-equilibrated with the sodium acetate buffer.

The PEG-coated waveguides were then incubated with the oxidized antibody solution in the sodium acetate buffer, pH 5.2, for 3 days at 4° C., then rinsed to remove unbound antibody.

The levels of non-specific absorption of antigen on waveguides prepared by this method were around 25–27%, which is considerably lower than that observed with prior art methods.

For the procedures detailed in Examples I–III and for which a comparison of results is given in Table I, the Fab' fragments used were derived from a murine anti-human chorionic gonadotrophin (anti-hCG) monoclonal IgG antibody. The parent monoclonal antibody was purified as described by van Erp et al. *J. Immunol. Methods*, 140:235–241 (1991). This mouse antibody, termed anti-hCG-A, is directed against a portion of the β-subunit of hCG (provided by Organon-Teknika of Boxtel, Netherlands). The whole monoclonal antibody anti-hCG-A was used in the experiments whose results are depicted in FIGS. 7–10.

F(ab')$_2$ fragments were produced by digestion with pepsin using the procedure described by Grey and Kunkel, "H Chain subgroups of myeloma proteins and normal 7S globulin," *J. Exp. Med.* 120:253–266, 1964. Following digestion, F(ab')2 fragments were reduced to Fab' fragments using dithiothrietol (DTT). Specifically, 33 mg of purified antibody and 1 mg pepsin (Sigma) were dissolved in 0.1M sodium acetate buffer (pH 4.2) and the digestion was carried out at 37° C. for 16 hours. The digestion was terminated by adjusting the pH of the reaction mixture to 8.0 with 2M tris base. The F(ab')$_2$ fraction was separated by gel permeation chromatography (Superdex Hiload, Pharmacia) using phosphate-buffered saline (PBS), pH 7.7, as eluent. Fab' fragments were prepared by reducing the F(ab')$_2$ fragments (1 mg/ml) with 1.75 mM DTT and 3.5 mM ethylenediamine tetraacetate (EDTA) in 0.17M tris buffer (pH 7.4) for 45 minutes at room temperature. After reduction, excess DTT was removed by gel permeation chromatography using a Sephadex G-25 column (Pharmacia) equilibrated in 0.1M sodium phosphate buffer (pH 6.0) containing 5 mM EDTA.

Figure 7A:
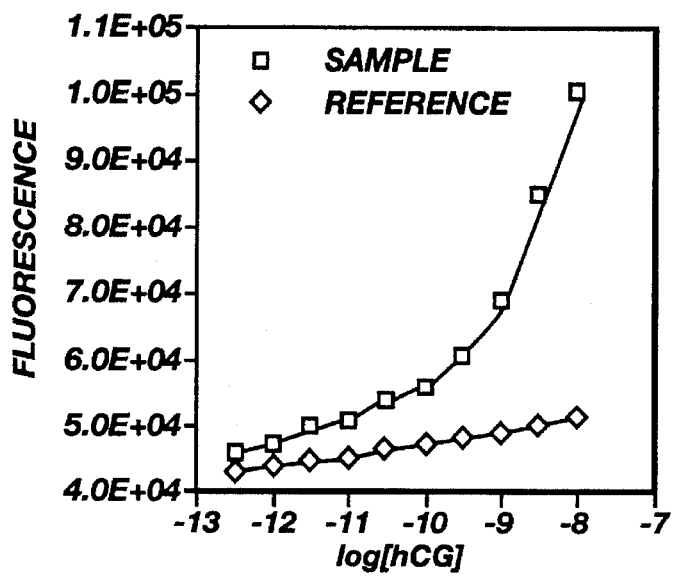
FIG. 7A is a chart depicting fluorescence intensity data from a sandwich fluoroimmunoassay for detecting an antibody, and performed with the apparatus of FIG. 1 according to a first assay format.
Figure 7B:
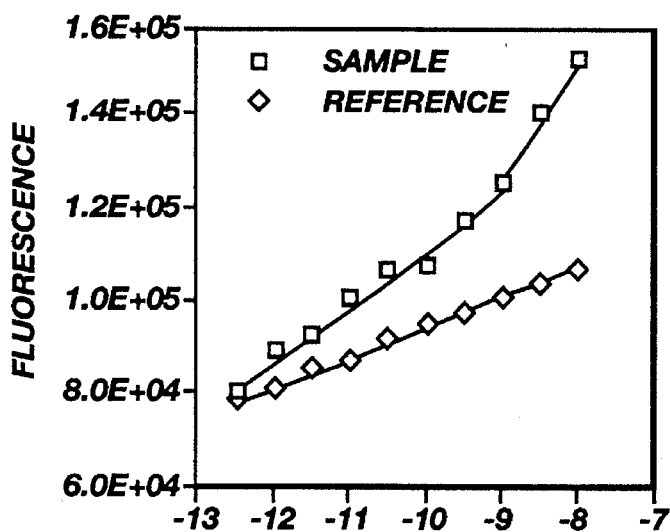
FIG. 7B is a chart depicting data from a sandwich fluoroimmunoassay performed with the apparatus of FIG. 1 according to an alternate assay format.
Figure 8:
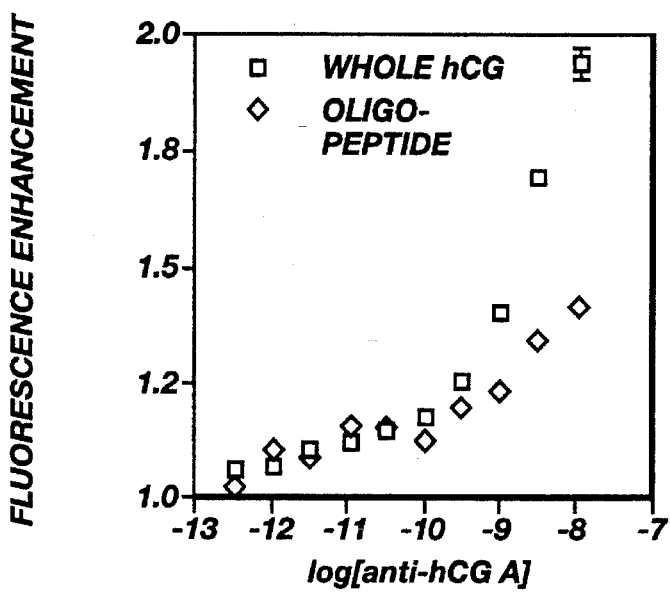
FIG. 8 is a chart comparing the fluorescence enhancement observed with the assay formats of FIGS. 7A and 7B.

FIGS. 7A, 7B and 8 are charts depicting fluorescence intensity data obtained using two alternate formats for performing a fluorescence immunoassay to detect an antibody. In these experiments, the detection of antibodies to human chorionic gonadotrophin (abbreviated hCG) was used as a model to determine which format provided the greatest sensitivity. It will be evident that the methods described could be adapted to the detection of any desired antibody in biological fluids such as plasma or serum, for example the detection of antibodies to proteins of viral and bacterial pathogens, depending only on obtaining the necessary antigen for use as the capture molecule.

For purposes of the tests shown in FIGS. 7 and 8, the antibody to be detected (the analyte) was chosen to be a monoclonal antibody to an hCG antigen designated hCG-A. The data of FIG. 7A were obtained with whole hCG molecules serving as the capture molecules (the antigen or analyte binding molecule) in the assay. The data of FIG. 7B were obtained using a hexapeptide constructed to selectively bind the hCG-A antigen, as the capture molecules. In both experiments, the tracer was a goat anti-mouse IgG labelled with tetramethylrhodamine (abbreviated TMR). For both assay formats, the capture molecule was biotinylated as described in Example II and immobilized on an avidin-coated silica substrate. The test antibody, anti-hCG A, was premixed with the tracer (goat anti-mouse IgG-TMR) in the test solution.

As will be understood by those in the art for a sandwich fluoroimmunoassay, the anti-hCG A antibody bound to the immobilized capture molecule, and the goat-anti-mouse igG-TMR tracer in turn bound to the mouse anti-hCG A antibody. In this way a fluorescent sandwich formed on the substrate surface with the TMR-portion of the tracer molecule being held within the region of evanescent excitation.

The immunoassays were performed using an interfacial fluorometer constructed at the University of Utah. Silica waveguides with the appropriate respective immobilized antigens were placed in the dual-channel flow-cell of FIG. 3. The two channels were used for sample and reference measurements, as described with respect to FIGS. 4A–C. The light source was the 514.5 nm emission of an air-cooled argon-ion laser. The laser beam was split into two parallel beams, which were focused with lenses into the two channels of the waveguide. Fluorescence emission was recorded from 520 to 620 nm using a momochromator connected to a computer-controlled CCD camera. The fluorescence spectrum was integrated from 560 to 600 nm to improve the signal-to-noise ratio. The following protocol was used in all experiments. Different concentrations of anti-hCG A were premixed with the tracer antibody (concentration fixed at $10^{-8}$M) and injected into the sample channel. A $10^{-8}$M concentration of tracer antibody was also injected into the reference channel as a control. The fluorescence intensity of the sample channel was plotted vs. anti-hCG A concentration and the fluorescence intensity of the reference channel was also plotted on the same set of axes (this is really a plot of the non-specific binding of the tracer antibody vs. time, since no anti-hCG A was injected into the reference channel). FIGS. 7A and 7B show the results for the sandwich binding of anti-hCG A to the immobilized hCG and the oligopeptide, respectively. FIG. 8 shows the corresponding fluorescence enhancements for both cases. The data from FIGS. 7A and 7B were normalized for background fluorescence and replotted as fluorescence enhancement ($F_{sample}$/Freference) versus log analyte concentration. The response curve was similar for both of the immobilized antigens (whole hCG and oligopeptide antigen) over a range of antibody concentrations from $10^{-13}$M to $10^{-10}$M. However, whole hCG gave better precision.

It is also evident from FIGS. 7A, 7B and 8 seen that analyte levels (anti-hCG A) as low as $10^{-13}$ molar were detectable with the assay. In a further embodiment, the tracer antibody concentration is reduced to $10^{-10}$M or less. This is expected to reduce background fluorescence due to non-specific adsorption of the tracer antibody and thereby further improve the sensitivity to $10^{-14}$M or better.

FIG. 9 depicts data obtained using an antibody as the capture molecule to detect an antigen, in a sandwich-type assay. As mentioned previously, two different antibodies are employed in a sandwich immunoassay—an immobilized capture antibody and a labelled tracer antibody in solution. Since the capture antibody and the tracer antibody must bind to distinct regions of the antigen, two different monoclonal antibodies which bind to different epitopes on the antigen are typically used in such assays. In addition to the anti-hCG-A, three other monoclonal anti-hCG antibodies (anti-hCG-B, anti-hCG-C and anti-hCG-D, respectively) were obtained from Organon Teknika which bound to different epitopes than did anti-hCG-A. Since only anti-hCG A (the others also bind to certain hormones related to hCG), only six of the twelve possible pairwise combinations of antibodies provide strict selectivity for hCG.

Figure 9A:
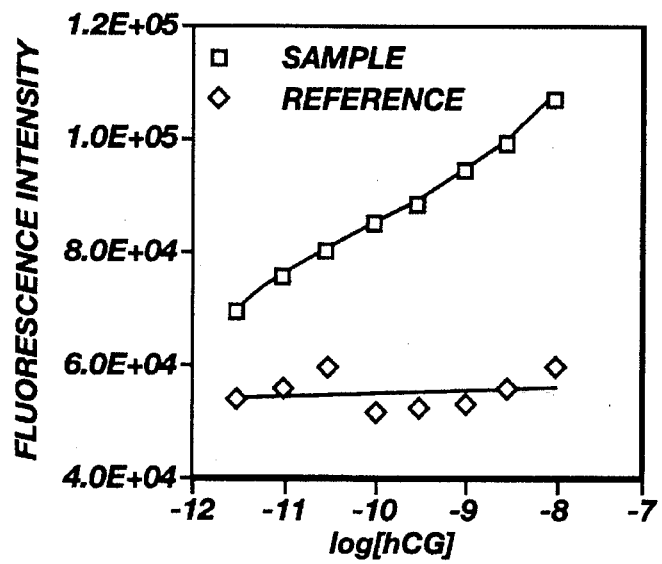
FIGS. 9A–F are charts depicting data from an alternate scheme for a sandwich fluoroimmunoassay for detecting an analyte using a corresponding antibody.
Figure 9B:
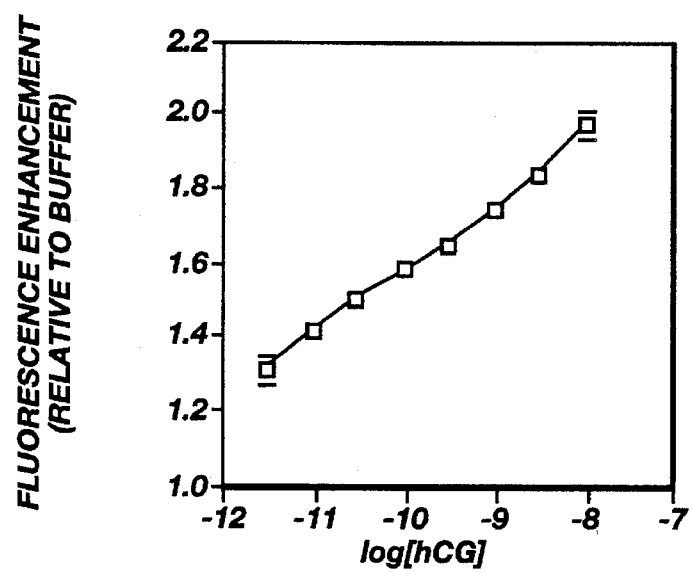
Figure 9C:
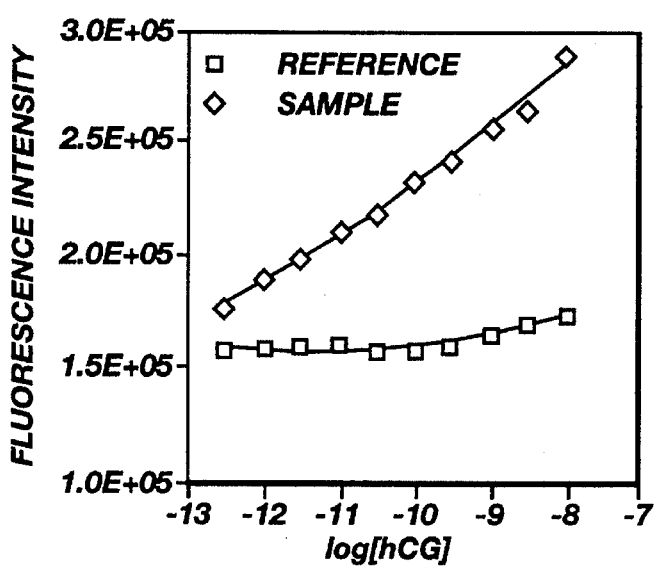
Figure 9D:
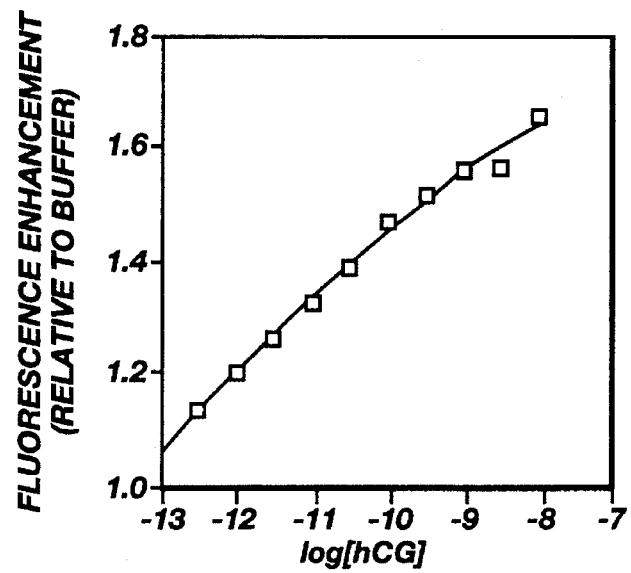
Figure 9E:
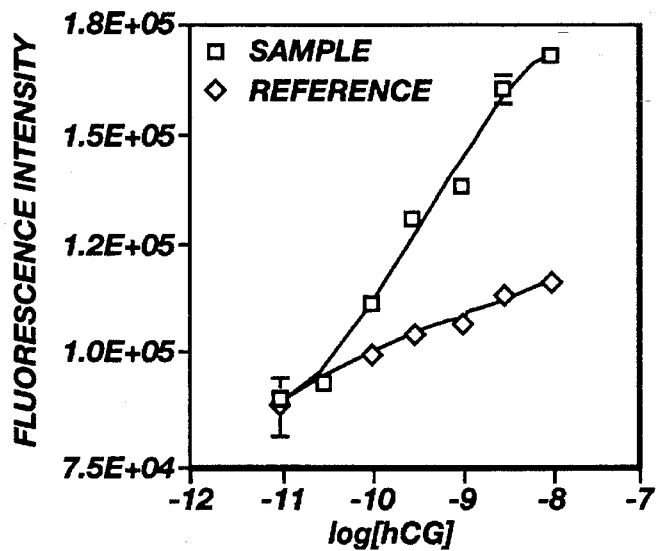
Figure 9F:
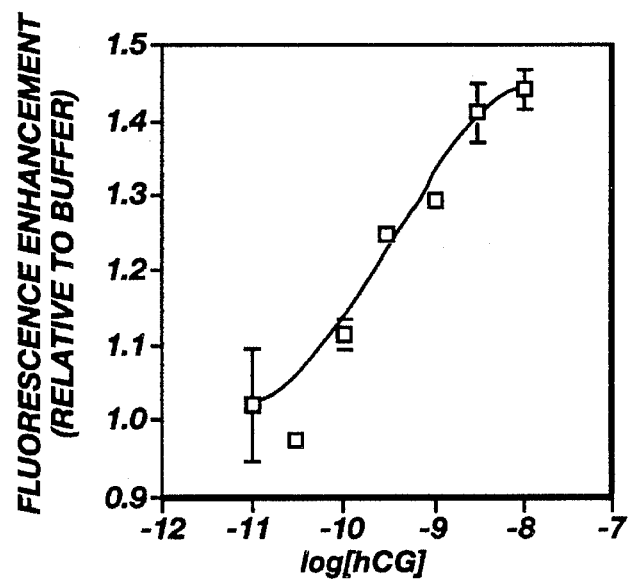

FIGS. 9A–F depict results obtained with different pairwise combinations, with Fab' fragments from anti-hCG A (Fab'-A) and immobilized to waveguides using the avidin-biotin coupling chemistry. Fab' fragments prepared from anti-hCG B, anti-hCG C and anti-hCG D were labeled with tetramethylrhodamine for use as tracer antibodies (designated Fab'-B, Fab'-C and Fab'-D, respectively). FIGS. 9A and 9B show results with Fab'-B as the tracer molecule. FIGS. 9C, 9D show results obtained using Fab'-C as the tracer molecule. FIGS. 9E, 9F show results obtained using Fab'-D as the tracer molecule. Presently, Fab'-B and Fab'-C are preferred for use as tracers in an hCG assay. The format using Fab'-A as the capture antibody was generally superior in sensitivity to the converse protocol, that is, to using Fab'-A as the tracer molecule and Fab'-B, -C or -D as the capture molecule.

Figure 10A:
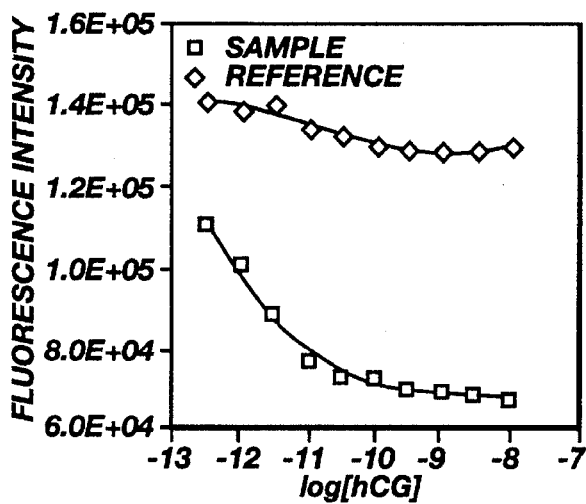
FIGS. 10A–D are charts depicting data from a displacement fluoroimmunoassay performed with the apparatus.
Figure 10B:
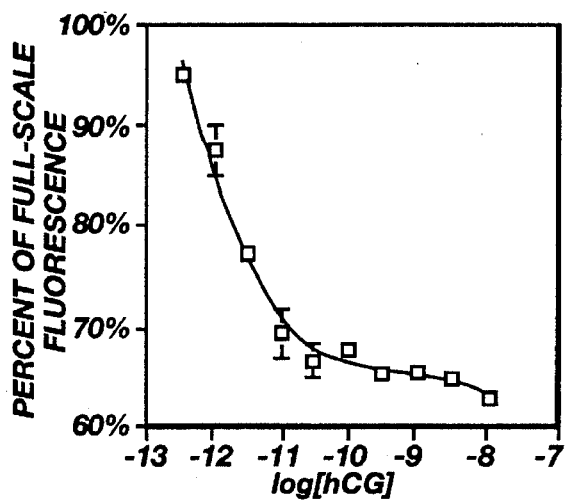
Figure 10C:
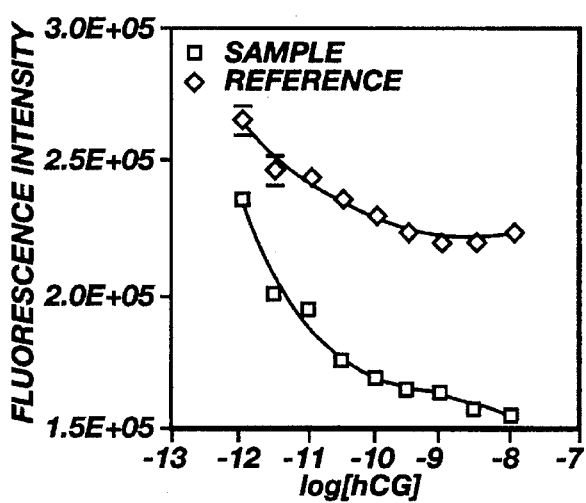
Figure 10D:
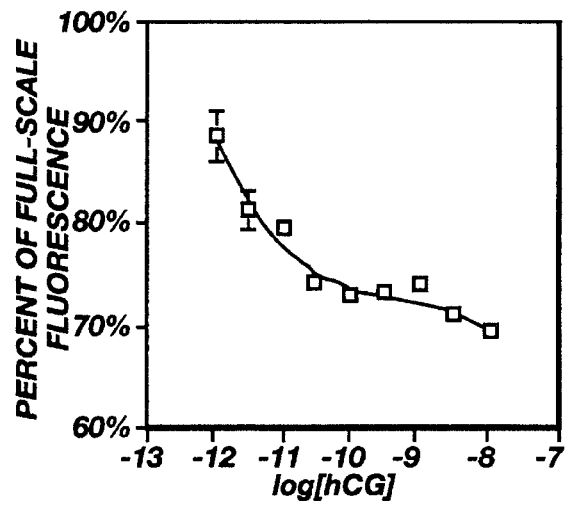

FIGS. 10A–D show data obtained from a competition or displacement assay. Fab'-A fragments were immobilized to waveguides using either the avidin-biotin chemistry (FIGS. 10A, 10B) or the hydrogel coupling chemistry (FIGS. 10C, 10D). The immobilized Fab'-A fragments were preloaded with the tracer oligopeptide at a concentration of $10^{-8}$M. Increasing concentrations of hCG were added to one channel of the flow cell (sample) and PBS buffer was added to the other (reference). For each coupling chemistry, the raw fluorescence intensities of the sample and reference channels are shown in the panels on the left (10A & 10C) and the percent of full-scale fluorescence (in the absence of hCG) are shown in the panels on the right (10B & 10D). The latter values were normalized for the change in reference fluorescence. Standard errors were plotted for all data points, but in some cases were smaller than the plot marks.

In some experiments for the purpose of characterizing the apparatus and assay system, fluorescein-BSA (BSA=bovine serum albumen) conjugates with an epitope density of nine were the analyte and the capture molecules were anti-BSA Fab' fragments. It was found that non-specific binding to the avidin-coated waveguide was acceptably low for antigen (analyte molecule) concentrations of less than about $10^{-5}$M, without a wash step.

At present the sandwich immunoassay is preferred for several reasons. First, detection of concentrations down to at least 0.1 picomolar can be demonstrated, as compared to picomolar concentrations for the competitive assay. Also, the instant sandwich immunoassay was capable of detecting concentrations ranging over five logs—from $10^{-8}$M to $10^{-13}$M. Thus, a single assay formulation using the sandwich procedure could serve for a variety of applications where different detection limits are required.

While the preceding experimental examples and results were obtained using hCG antigen—anti-hCG antibody and fluorescein-anti-fluorescein antibody systems, it will be understood by those skilled that the apparatus and the biosensor, as well as the site-specific waveguide-coupling methods and assay formats, all are applicable to assays for any antigen or antibody for which the requisite reagents such as appropriate capture molecules can be obtained, without undue experimentation. It will further be understood that while tetra-rhodamine, fluorescein, and cyanine dyes are specifically mentioned as useful for labelling of tracer molecules, the apparatus and methods can also be useful with other fluorescent dyes capable of being conjugated to the desired tracer molecule.

It will further be recognized that various modifications and substitutions may be made to the apparatus and the biosensor as described herein, without departing from the concept and spirit of the invention.

We claim:

1. A fluorescence immunoassay, comprising the steps of:

providing a solid substrate formed of a material selected from the group consisting of silica-based materials constructed for propagation of light by total internal reflectance, and having a surface with a plurality of capture molecules indirectly immobilized thereon via a coating comprising 3-aminopropyltriethoxy silane bonded to said substrate and a plurality of polymerized hydrophilic polymer chains selected from the group consisting of hydrogel formed of polymethacryloyl and polyethyleneglycol, said hydrophilic polymer chains coupled to said 3-aminopropyltriethoxy silane, said capture molecules having a binding site which selectively binds a selected analyte;

providing a light source operable to emit a light beam in a desired wavelength range and positioned to send light into said substrate;

providing detection means operably disposed for detecting fluorescence emitted from the solid substrate;

providing a sample comprising a buffer and a plurality of molecules of a selected analyte;

providing a plurality of tracer molecules which are operable to emit fluorescence in response to stimulation by light from the light source, said binding sites on said capture molecules also selectively bind to the tracer molecules;

combining the sample with the tracer molecules to produce a test solution;

placing the test solution in contact with the solid substrate while operating said light source to direct light into the solid substrate;

selectively detecting fluorescent light emitted from bound tracer molecules; and measuring the level fluorescence emitted to determine the presence of analyte.

2. The fluorescence immunoassay of claim 1, wherein said step of providing a solid substrate having capture molecules immobilized thereon includes the steps of:

coating the substrate surface with the 3-aminopropyltriethoxy silane to produce a first layer;

applying a second layer to said first layer, said second layer selected from the group consisting of: PEG polymers modified to covalently couple to said first layer, said PEG polymers further having an attached biotin moiety, and a hydrogel composed of polymethacryloyl polymers; and modifying said capture molecules to produce activated capture molecules constructed to bind to the coating; and treating the coating with the activated capture molecules under conditions to cause the activated capture molecules to couple to the coating.

3. The assay of claim 2, wherein said coating inhibits non-specific binding to less than about 10% of the specific binding of the tracer molecules to the substrate.

4. The assay of claim 2, wherein said second layer provides a plurality of free maleimido groups.

5. A fluorescence immunoassay, comprising the steps of:

providing a solid substrate formed from silica-based materials constructed for propagation of light by total internal reflection, and having a surface with a plurality of capture molecules indirectly immobilized thereon via a coating comprising 3-aminopropyltriethoxy silane bonded to said substrate and a plurality of polymerized hydrophilic polymer chains selected from the group consisting of biotinylated polyethylene glycol of molecular weight between about 2000 and 5000, PEG polymers of molecular weight between about 2000 and about 5000, and polymethacryloyl polymers of molecular weight between about 2000 and about 5000 coupled to said 3-aminopropyltriethoxy silane, said capture molecules having a binding site which selectively binds a selected analyte;

providing a light source operable to emit a light beam in a desired wavelength range and positioned to send light into said substrate;

providing detection means operably disposed for detecting fluorescence emitted from the solid substrate;

providing a sample comprising a buffer and a plurality of molecules of a selected analyte;

providing a plurality of tracer molecules which are operable to emit fluorescence in response to stimulation by light from the light source, said binding sites on said capture molecules also selectively bind to the tracer molecules;

combining the sample with the tracer molecules to produce a test solution;

placing the test solution in contact with the solid substrate while operating said light source to direct light into the solid substrate;

selectively detecting fluorescent light emitted from bound tracer molecules; and measuring the level fluorescence emitted to determine the presence of analyte.

6. A biosensor for use with a fluorescence immunoassay system having a light source producing a light beam, means for directing the light beam to irradiate a biosensor, and detection means for detecting a tracer light signal reflective of an amount of analyte in a test sample in contact with the biosensor, the biosensor comprising:

reservoir means for holding one or more test solutions, comprising at least one reservoir having walls;

an optical substrate constructed for propagation of light by total internal reflectance, and constituting one of said walls;

a coating comprising 3-aminopropyltriethoxy silane bonded to or avidin adsorbed on said optical substrate and a plurality of polymerized hydrophilic polymer chains selected from the group consisting of biotinylated polyethylene glycol, PEG polymers, and polymethacryloyl polymers, each of said polymerized hydrophilic polymer chains carrying a covalent binding moiety constructed to react with a selected complementary moiety; and a plurality of analyte-binding molecules constructed to specifically bind an analyte, and including said complementary moiety and attached thereby to said chains; said coating constructed to limit nonspecific adhesion of protein thereto to less than about 10% of the specific binding of the analyte to said analyte-binding molecule.

7. The biosensor of claim 6, wherein said coating is selected from the group consisting of: hydrogel formed of polymethacryloyl polymers of molecular weight between about 2000 and about 5000, polyethyleneglycol of molecular weight between about 2000 and about 5000, and biotinylated polyethyleneglycol.

8. The biosensor of claim 6, wherein said polymerized hydrophilic polymer chains consist of polyethylene glycol and polymethacryloyl polymers.

9. A kit useful for a solid state immunoassay, comprising an optical substrate constructed for propagation of light by total internal reflectance, and formed of a material selected from the group consisting of: silica-based optical materials including glass and quartz; said substrate having a surface coated with a coating comprising 3-aminopropyltriethoxy silane adsorbed on said surface and a plurality of hydrophilic polymers selected from the group consisting of polymethacryloyl polymers, polyethyleneglycol polymers, and biotinylated polyethyleneglycol, said hydrophilic polymers covalently bound to said 3-aminopropyltriethoxy silane; and a plurality of capture molecules coupled to said coating, said capture molecules each being constructed to specifically bind an analyte.

10. The kit of claim 9, wherein said non-specific binding level is less than about 2% of said specific binding level.

11. The kit of claim 9, further including at least one tracer molecule constructed to bind with specificity to the analyte, and having a covalently-coupled fluorescent moiety.

12. The kit of claim 11, wherein said capture molecule and said tracer molecule are both derived from a member of an antibody-antigen pair, and the other member of said antibody-antigen pair is said analyte.

13. The kit of claim 9, wherein said capture molecule is a Fab' fragment formed by treating a whole antibody with trypsin to produce an antibody fragment cleaved at a cleavage site, and treating said cleaved antibody with a reducing agent to form a reactive thiol group at said cleavage site.

14. The kit of claim 7, wherein said capture molecule has a thiol group reactively disposed thereon, wherein said capture molecule is covalently coupled to said coating via said thiol group and at least about 70% of said capture molecules have analyte capture sites which are available for binding said analyte, and wherein said substrate has a plurality of capture molecules immobilized thereon.

15. The kit of claim 9, wherein said coating comprises two layers, said first layer being applied directly to said surface and being selected from the group consisting of: aminopropyltriethoxysilane treated with glutaraldehyde, and avidin; and wherein said second layer is selected from the group consisting of: biotinylated PEG, PEG polymers of molecular weight between about 2000 and about 5000, and polymethacryloyl polymers of molecular weight between about 2000 and about 5000.

16. The kit of claim 9, wherein said optical substrate has opposing ends, and further including a lens integrally adapted to said optical substrate at one of said ends, and constructed to focus a light beam into said optical substrate for propagation therein.

17. The kit of claim 9, wherein said coating comprises two layers, said first layer being applied directly to said surface and being selected from the group consisting of: aminopropyltriethoxysilane and avidin; and said second layer being applied on said first layer and being selected from the group consisting of: biotinylated polyethylene glycol, PEG polymers of molecular weight between about 2000 and about 5000, and polymethacryloyl polymers.

18. A kit useful for a solid state immunoassay, comprising a substrate element constructed for propagation of light by total internal reflectance; said substrate element having a surface coated with a coating comprising 3-aminopropyltriethoxy silane bonded to or avidin adsorbed on said optical substrate and a plurality of polymerized hydrophilic polymer chains selected from the group consisting of biotinylated polyethylene glycol, polyethylene glycol polymers, and polymethacryloyl polymers; said polymerized hydrophilic polymer chains each carrying a covalent binding moiety constructed to react with a selected complementary moiety; and a plurality of capture molecules each constructed to specifically bind an analyte and each having a single said complementary moiety, wherein at least about 70% of said capture molecules have analyte capture sites which are available for binding the analyte, and wherein said capture molecules are covalently coupled to said coating via said complementary moiety and immobilized to said surface.

19. The kit of claim 18, wherein said polymerized hydrophilic polymer chains are selected from the group consisting of: polymethacryloyl polymers, avidin, and polyethyleneglycol polymers.

20. The kit of claim 9, wherein said capture molecule is a Fab' 'fragment formed by treating a whole antibody with trypsin to produce an antibody fragment cleaved at a cleavage site, and treating said cleaved antibody with a reducing agent to form a reactive thiol group at said cleavage site.

21. The kit of claim 18, wherein said capture molecule has a biotin moiety coupled thereto.

22. A substrate element for use in a biochemical binding assay of the type in which an analyte is detected by its mediation of the specific binding of a tracer molecule to a surface on which a capture molecule which specifically binds the analyte is immobilized, prepared by the steps of:
   providing a substrate element formed of a silica-based optical material;
   reacting 3-aminopropyltriethoxy silane with a surface of said substrate element;
   coupling a plurality of polymerized hydrophilic polymer chains selected from the group consisting of a hydrogel formed of polymethacryloyl and polyethylene glycol to said 3-aminopropyltriethoxy silane; and
   coupling capture molecules which specifically bind to said analyte to said plurality of hydrophilic polymer chains, wherein said substrate element provides a level of non-specific binding of the tracer molecule which is less than about 10% of the level of non-specific binding of the tracer molecule.

23. The biosensor of claim 22, wherein said coating is aminopropylsilane or avidin.

24. An apparatus for performance of a biochemical binding assay, comprising
   a light source providing a light beam in a desired wavelength range;
   a biosensor including
      a reservoir constructed for containing a sample solution to be tested for presence of an analyte,
      a waveguide substrate constructed for propagation of light by total internal reflectance, and having at least one surface disposed within said reservoir in contact with said sample solution,
      a reagent reacted to said at least one surface of said waveguide substrate, said reagent creating a grafting surface,
      a coating comprising polymerized hydrophilic polymer chains selected from the group consisting of polyethylene glycol polymers, and polymethacryloyl polymers, said hydrophilic polymer chains being attached to extend from said waveguide substrate via said reagent, and
      a plurality of capture molecules immobilized to said at least one surface via said coating, said capture molecules being constructed to specifically bind said analyte or a tracer molecule;
   channeling means operably associated with said light source and said biosensor for directing light from said light source to irradiate said waveguide substrate; and
   detection means operably disposed for detecting a light signal resulting from bound tracer molecules on said at least one surface of said waveguide substrate.

25. The apparatus of claim 24, wherein said polymer chains further have covalently attaching functional groups attached thereto, and said capture molecules are covalently coupled to said covalently attaching functional groups.

26. The apparatus of claim 25, wherein said surface has a plurality of capture molecules immobilized thereon, and wherein at least about 70% of said capture molecules have analyte capture sites which are available for binding said analyte.

27. The apparatus of claim 25, wherein said covalently attaching functional group is a maleimido group.

28. The apparatus of claim 27, wherein said capture molecule is a Fab' fragment formed by treating a whole antibody with trypsin to produce an antibody fragment cleaved at a cleavage site, and treating said cleaved antibody with a reducing agent to form a reactive thiol group at said cleavage site.

29. An optical substrate for use in a biochemical binding assay of the type is which an analyte is detected by its mediation of the specific binding of a tracer molecule to a surface on which a capture molecule which specifically binds the analyte is immobilized, comprising:

an optical element formed of an optical plastic or a silica-based optical material;

a reagent reacted to said optical element;

a coating attached to said optical element via said reagent and comprising a plurality of polymerized hydrophilic polymer chains selected from the group consisting of biotinylated polyethylene glycol, polyethylene glycol polymers, and polymethacryloyl polymers, each of said chains carrying a covalent binding moiety constructed to react with a selected complementary moiety selected from the group consisting of a thiol group and an oxidized carbohydrate moiety; and a plurality of analyte-binding molecules each constructed to specifically bind an analyte, and including said complementary moiety and attached thereby to said chains.

30. The optical substrate of claim 29, wherein at least about 70% of said capture molecules are reactively available for binding said analyte.

31. The optical substrate of claim 29, wherein said oxidized carbohydrate moiety is formed by treating a whole antibody with sodium metaperiodate.

* * * * *

UNITED STATES PATENT AND TRADEMARK OFFICE
CERTIFICATE OF CORRECTION

PATENT NO. : 5,512,492
DATED : April 30, 1996
INVENTOR(S) : Herron et al.

It is certified that error appears in the above-indentified patent and that said Letters Patent is hereby corrected as shown below:

In col. 4, line 6, after "is" insert --a--;

In col. 6, line 27, change "124" to --122--;

In col. 8, line 10, after "glass" insert --, the index of refraction--;

In col. 8, line 51, after "corrected" delete "for";

In col. 9, line 7, change "slot" to --waveguide--;

In col. 9, line 26, after "type" insert --of--;

In col. 9, line 66, after "then" delete "be";

In col. 12, line 61, after "powder" insert --was--;

In cols. 13-14, top table, 5th column from the left, on the 10th printed line under the column heading, change "0,01" to --0.01--;

In col. 15, Table III, in the title, change "Fragmebts" to --Fragments--;

In col. 15, line 55, change "F(ab')2" to --F(ab')$_2$--;

In col. 17, line 26, after "8" delete "seen";

In col. 19, line 8, change "bind" to --binding--;

In col. 19, line 17, after "level" insert --of--;

In col. 20, line 2, change "bind" to --binding--;

In col. 20, line 52, delete the colon after "of";

In col. 20, line 53, after "quartz" change the semicolon to a comma;

UNITED STATES PATENT AND TRADEMARK OFFICE
CERTIFICATE OF CORRECTION

PATENT NO. : 5,512,492
DATED : April 30, 1996
INVENTOR(S) : Herron et al.

It is certified that error appears in the above-indentified patent and that said Letters Patent is hereby corrected as shown below:

In col. 21, line 8, delete the comma after "site";

In col. 21, line 10, change "claim 7" to --claim 9--;

In col. 21, line 19, delete the colon after "of";

In col. 21, line 20, delete the comma after "glutaraldehyde";

In col. 21, line 61, change "claim 9" to --claim 19--;

In col. 21, line 64, delete the comma after "site";

In col. 22, line 24, insert a colon after "comprising";

In col. 23, line 1, delete the comma after "site";

In col. 23, line 5, after "type" change "is" to --in--;

Signed and Sealed this

Eighteenth Day of February, 1997

Attest:

BRUCE LEHMAN

*Attesting Officer*  *Commissioner of Patents and Trademarks*